US007847120B2

(12) United States Patent
Quick et al.

(10) Patent No.: US 7,847,120 B2
(45) Date of Patent: Dec. 7, 2010

(54) COMPOSITIONS OF ALLOSTERIC HEMOGLOBIN MODIFIERS AND METHODS OF MAKING THE SAME

(75) Inventors: Al Quick, Aurora, CO (US); Antonio M. Santos, Columbus, NJ (US); Alexandre J G G Carvalho, Lisbon (PT); Douglas G. Johnson, Arvada, CO (US); Jeffrey B. Etter, Boulder, CO (US); Christopher Murray, Arlington, MA (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 1281 days.

(21) Appl. No.: 11/112,389

(22) Filed: Apr. 22, 2005

(65) Prior Publication Data

US 2005/0239893 A1     Oct. 27, 2005

Related U.S. Application Data

(60) Provisional application No. 60/564,721, filed on Apr. 22, 2004.

(51) Int. Cl.
*C07C 229/00* (2006.01)
*C07C 65/03* (2006.01)
(52) U.S. Cl. .................................... 562/457; 562/471
(58) Field of Classification Search .................. None
See application file for complete search history.

(56) References Cited

U.S. PATENT DOCUMENTS

| | | | |
|---|---|---|---|
| 5,049,695 A | | 9/1991 | Abraham et al. |
| 5,122,539 A | * | 6/1992 | Abraham et al. ............ 514/563 |
| 5,248,785 A | | 9/1993 | Abraham et al. |
| 5,250,701 A | | 10/1993 | Abraham et al. |
| 5,290,803 A | | 3/1994 | Abraham et al. |
| 5,382,680 A | | 1/1995 | Abraham et al. |
| 5,432,191 A | | 7/1995 | Abraham et al. |
| 5,525,630 A | | 6/1996 | Hoffman |
| 5,591,892 A | | 1/1997 | Abraham et al. |
| 5,648,375 A | | 7/1997 | Abraham |
| 5,661,182 A | | 8/1997 | Abraham et al. |
| 5,665,382 A | | 9/1997 | Grinstaff |
| 5,677,330 A | | 10/1997 | Abraham et al. |
| 5,705,521 A | | 1/1998 | Abraham |
| 5,731,454 A | | 3/1998 | Abraham et al. |
| 5,827,888 A | | 10/1998 | Abraham et al. |
| 5,927,283 A | | 7/1999 | Abraham et al. |
| 6,486,342 B1 | | 11/2002 | Abraham et al. |
| 2003/0232887 A1 | | 12/2003 | Johnson et al. |

FOREIGN PATENT DOCUMENTS

| DE | 24 32 560 | | 1/1976 |
|---|---|---|---|
| DE | 2432560 | * | 1/1976 |
| WO | WO 97/34594 | | 9/1997 |
| WO | WO 01/14316 | | 3/2001 |
| WO | WO03/086324 | | 10/2003 |
| WO | WO 03/092700 | | 11/2003 |

OTHER PUBLICATIONS

Abraham et al. (1992) *Biochemistry* 31:9141-9149.
Abraham et al. (1998) *Med. Chem. Res.* 8:478-486.
Amorino et al. (2001) *Radiation Research* 156:294-300.
Grella et al. (2000) *Journal Med. Chem.* 43:4726-4737.
Kavanagh et al. (2001) *Int. J. Radiation Oncology Biol. Phys.* 49:1133-1139.
Muguruma et al. (Jul. 1999) *LC-GC International*, pp. 432-436.
Pagel et al. (1998) *Journal of Pharmacology and Experimental Therapeutics* 285:1-8.
Randad et al. (1991) *J. Med. Chem.* 34:752-757.
Rockwell and Kelley (1998) *Rad. Oncol. Invest.* 6:199-208.
Safo et al. (2001) *Protein Science* 10:951-957.
Sarraf-Yazdi et al. (1999) *Brain Research* 826:172-180.
Steffen (1998) *Oxygen Transport to Tissue XX* 454:653-661.
Teicher et al. (1996) *Drug Dev. Res.* 38(1):1-11.
Teicher et al. (1998) *Cancer Chemother. Phamacol.* 42:24-30.
Wahr et al. (2001) *Anesth. Analg* 95:615-620.
Watson et al. (1997) *Stroke* 28:1624-1630.
Wireko et al. (1991) *Journal of Medicinal Chemistry* 34:758-767.
Steffen et al. Allosteric Modification of Hemoglobin by RSR13 as a Therapeutic Strategy. Advances in Experimental Medicine and Biology. (2003) 530:249-259.
Chang et al. Diagnosis and Management of Central Nervous System Metastases from Breast Cancer. The Oncologist. (2003) 8 398-410.
Papassotiriou et al. (1998) Experimental Hematology 26:922-926.
Rowinsky (1999) Oncology 10:61-70.

* cited by examiner

*Primary Examiner*—Karl J Puttlitz
(74) *Attorney, Agent, or Firm*—Whitham Curtis Christofferson & Cook, PC

(57) ABSTRACT

The present invention provides novel compositions of allosteric hemoglobin modifiers which are substantially free of impurities, specifically polymeric impurities. In one embodiment, the novel compositions contain an allosteric hemoglobin modifier compound and less than 100 ppm of the polymeric impurities generated during the preparation of this compound. Included in the present invention are novel methods for preparing allosteric hemoglobin modifiers that are substantially free of polymeric impurities. Also included in the present invention are improved methods for the purification of the product formed by the method of this invention. The novel methods of purification comprise extracting the crude composition with a water immiscible or partially immiscible solvent such as methylisobutyl ketone (MIBK) to lower amounts of impurities, specifically polymeric impurities. Also included are methods to reduce impurities by recrystallization of the crude synthesized product, followed by filtration of the recrystallized product. The present invention also includes the products made by the processes of the invention and methods for analyzing compositions comprised of these products.

40 Claims, 10 Drawing Sheets

COMPOSITIONS OF ALLOSTERIC HEMOGLOBIN MODIFIERS AND METHODS OF MAKING THE SAME

RELATED APPLICATIONS

This application claims the benefit of U.S. Provisional Patent Application Ser. No. 60/564,721, filed Apr. 22, 2004, entitled "Compositions of Allosteric Hemoglobin Modifiers and Methods of Making the Same," which is incorporated herein by reference in its entirety.

FIELD OF THE INVENTION

The present invention relates to compositions of allosteric hemoglobin modifier compounds having low levels of impurities. The invention also relates to novel methods of preparing such compositions. Included in the present invention are improved methods for the purification of compositions of allosteric hemoglobin modifier compounds. Also included in the present invention is a method for analyzing compositions of allosteric hemoglobin modifier compounds, which enables detection and quantification of impurities.

BACKGROUND OF THE INVENTION

Hemoglobin is a tetrameric protein which delivers oxygen via an allosteric mechanism. There are four binding sites for oxygen on the hemoglobin molecule, as each protein chain contains one heme group. Each heme group contains a substituted porphyrin and a central iron atom. The iron atom in heme can be in the ferrous (+2) or ferric (+3) state, but only the ferrous form binds oxygen. The ferrous-oxygen bond is readily reversible. The binding of the first $O_2$ molecule to hemoglobin enhances the binding of additional $O_2$ to the same hemoglobin molecule. In other words, $O_2$ binds cooperatively to hemoglobin. Thus, binding of the first oxygen to a heme requires much greater energy than the second oxygen molecule, binding of the third oxygen requires even less energy, and the fourth oxygen requires the lowest energy for binding. Hemoglobin A, the principal hemoglobin in adults consists of two $\alpha$ and two $\beta$ subunits arranged with a two-fold symmetry. The $\alpha$ and $\beta$ dimers rotate during oxygen release to open a large central water cavity. The allosteric transition that involves the movement of the alpha beta dimer takes place between the binding of the third and fourth oxygen.

Using well-known equipment such as the AMINCO™ HEM-O-SCAN, an oxygen dissociation curve can be plotted to determine the affinity and degree of cooperativity (allosteric action) of hemoglobin. In the plot, the Y-axis represents the percent of hemoglobin oxygenation and the X-axis represents the partial pressure of oxygen in millimeters of mercury (mm Hg). If a horizontal line is drawn from the 50% oxygen saturation point and a vertical line is drawn from the intersection point of the horizontal line with the curve to the partial pressure X-axis, a value commonly known as the $P_{50}$ is determined. This is the partial pressure (mm Hg) at which the hemoglobin sample is 50% saturated with oxygen. Under physiological conditions (i.e. 37° C., pH 7.4, and a partial pressure of carbon dioxide of 40 mm Hg), the $P_{50}$ value for normal adult hemoglobin is around 26.5 mm Hg. If a lower than normal $P_{50}$ value is obtained for the hemoglobin being tested, the oxygen dissociation curve is considered to be "left-shifted" and the presence of high affinity hemoglobin is indicated. Conversely, if a higher than normal $P_{50}$ value is obtained for the hemoglobin being tested, the oxygen dissociation curve is considered to be "right-shifted" and the presence of low affinity hemoglobin is indicated. Such low affinity hemoglobin will lose oxygen more easily at lower pressures of oxygen, and therefore may be useful to deliver oxygen to tissues more efficiently.

It has been suggested that influencing the allosteric equilibrium of hemoglobin may be a viable method to treat diseases that are influenced by oxygen delivery. For example, the conversion of hemoglobin to a high affinity state is generally regarded to be beneficial in treating problems associated with deoxyhemoglobin S (sickle cell anemia.). The conversion of hemoglobin to a low affinity state is believed to be of general utility in a variety of disease states in which tissues suffer from low oxygen tension, such as ischemia, radio-sensitization of tumors, carbon monoxide poisoning, fetal oxygen delivery and the restoration of the oxygen affinity of stored blood.

FIGS. 1A-1D depict the chemical structures of a variety of compounds which have a "right-shifting" allosteric effect on hemoglobin (referred to herein as "allosteric hemoglobin modifier compounds" or "allosteric effector compounds"). The family of compounds represented by the general structure illustrated in FIG. 1D (referred to as "RSR compounds"), are representative of a large family of compounds having a strong allosteric effect. For example, one compound in this family, 2-[4-((((3,5-dimethylphenyl)amino)carbonyl)methyl)phenoxy]-2-methyl propionic acid (efaproxiral, also referred to as RSR13), which has the following structure, when $X^+$ is $H^+$:

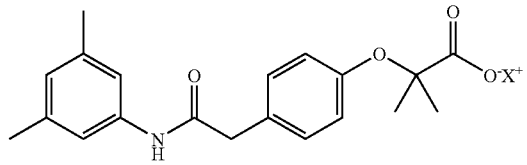

5 is an allosteric effector of hemoglobin, and has been shown to enhance tissue oxygenation in vivo. In general, efaproxiral is administered as a physiologically acceptable salt, such as the monosodium salt; that is, $X^+$ is $Na^+$. Efaproxiral induces allosteric modification of hemoglobin, such that its binding affinity for oxygen is decreased, resulting in increased oxygen distribution to tissues by erythrocytes. Efaproxiral has been reported to enhance fractionated radiation therapy in mice bearing the Lewis lung carcinoma. See Teicher (1996) Drug Dev. Res. 38:1-11. Enhancement of the effect of radiation was observed in EMT6 mouse mammary tumors by treatment with efaproxiral plus oxygen breathing, with the absence of enhanced radiation effects in normal tissues. Rockwell and Kelley (1998) Rad. Oncol. Invest. 6:199-208. Additionally, mouse fibrosarcoma tumor growth has been shown to be reduced by the combination of efaproxiral and radiation relative to radiation alone. See Teicher (1996) Drug Dev. Res. 38: 1-11; Khandelwal et al. (1996) Rad. Oncol. Invest. 4:51-59. This family of compounds, together with their utility and methods for using them are described in a number of patents including, U.S. Pat. No. 5,661,182, issued Aug. 26, 1997, U.S. Pat. No. 5,290,803, issued Mar. 1, 1994, U.S. Pat. No. 5,382,680, issued Jan. 17, 1995, U.S. Pat. No. 5,432,191, issued Jul. 11, 1995, U.S. Pat. No. 5,648,375, issued Jul. 15, 1997, U.S. Pat. No. 5,677,330, issued Oct. 14, 1997, U.S. Pat. No. 5,731,454, issued Mar. 24, 1998, U.S. Pat. No. 5,122,539, issued Jun. 16, 1992, U.S. Pat. No. 5,927,283, issued Jul. 27, 1999, U.S. Pat. No. 5,827,888, issued Oct. 27, 1998, U.S. Pat. No. 5,049,695, issued Sep. 17, 1991, U.S. Pat. No. 5,591,892, issued Jan. 7, 1997, U.S. Pat. No. 5,049,695, issued Sep. 17, 1991, U.S. Pat. No. 5,250,701, issued Oct. 5, 1993, U.S. Pat. No. 5,248,785, issued Sep. 28, 1993, U.S. Pat. No. 5,705,521, issued Jan. 6, 1998, and U.S. Pat. No. 5,525,630, issued Jun. 11, 1996. Each of these references is specifically incorporated herein by reference in its entirety.

As a result of the general utility and importance of these compounds a number of methods have been developed to synthesize them. Two of the principal methods developed to date are compared in FIG. 2 using the synthesis of the sodium salt of 2-[4-((((3,5-dimethylphenyl)amino)carbonyl)methyl)phenoxy]-2-methyl propionic acid (also referred to herein as efaproxiral sodium and efaproxiral-Na) (5), for purposes of illustration. With reference to FIG. 2, in the first method developed (referred to as Process A), efaproxiral-Na (5) was synthesized as the free acid (6), which was then treated with base to provide the sodium salt (5). (Randad et al. (1991) J. Med. Chem. 34:752-757). In the second method (referred to as Process B), this compound was synthesized as the ethyl ester (4), which was then saponified to provide the sodium salt (5). (Witt et al., DE 2,432,560, published Jan. 22, 1976). Process A is highly exothermic, not easily amenable to commercial scale manufacture and uses a halogenated hydrocarbon solvent. Process B eliminates the use of a halogenated hydrocarbon solvent and is more amenable to commercial scale manufacture and thus is the preferred method. The primary drawback of Process B, however, is the unexpected generation of the polymeric impurity poly(ethyl methacrylate) and precursors to this compound, which are referred to herein collectively as PEM, which is formed in Step 2 via the following mechanism.

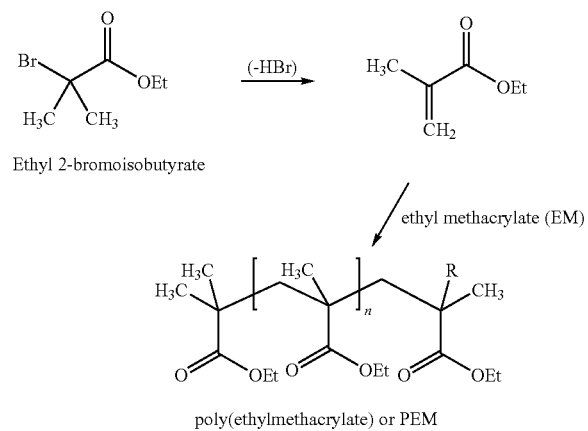

In the manufacture of the efaproxiral sodium (5) via Process B poly(ethyl methacrylate) is typically formed in concentrations of from approximately 0.5% (5000 parts per million (ppm)) to 9% (90,000 ppm) by weight.

Despite the general utility and importance of these compounds in treating disease, problems remain in generating pharmaceutical grade compositions. Specifically, the compounds are administered to patients in a sterile intravenous (IV) solution preparation. In the process of testing these compounds, difficulty with the drug product manufacturing (IV solution formation) has been traced to the PEM byproduct generated during their synthesis as outlined above. Thus, there is a need for methods to reduce the level of polymeric impurity in preparations of allosteric hemoglobin modifier compounds in order for use in patients. There also remains a need for compositions of allosteric hemoglobin modifying compounds with lower amounts of impurities in general. The present invention provides an improved process for making highly pure allosteric effector compounds.

Another problem associated with the prior art methods is that there is currently no effective way to measure the low levels of impurities capable of causing failure in the IV solutions prepared from compositions, which are comprised of these compounds. As noted above, a particularly undesirable impurity is PEM. Prior art methods for measuring PEM are deficient in several respects, particularly in that they are unable to detect very low levels of PEM. Current methods for detecting and measuring PEM include $^1$H NMR, gel permeation chromatography (GPC) or size exclusion chromatography (SEC); MALDI-TOF mass spectrometry; ultraviolet (UV) analysis; and infrared (IR) analysis. The latter two techniques are accurate for mixtures containing ≧2-4% PEM w/w in efaproxiral ethyl ester (4) or efaproxiral sodium (5). The former techniques can be used for determining the concentration of ≧0.5% w/w PEM. For example, to analyze intermediates with ≧0.5% w/w PEM, $^1$H NMR can be used by comparing the integration of the PEM methylene proton signal to the ethoxy-methylene proton signal of the efaproxiral ethyl ester (4). By multiplying the appropriate molecular weights to the respective signals of the PEM and efaproxiral ethyl ester one can develop a formula for determining the percent weight/weight (% w/w) of PEM. Muguruma et al. describe a method for the quantitative analysis of poly(methylmethacrylate) (PMMA) in drug substances using pyrolysis-gas chromatography (PY/GC). Using this method, Muguruma were able to detect levels of PMMA ≧0.1 wt % with a precision of approximately 4.5% at a level of 0.1%. (Mugurma et al. (July 1999) LC-GC International, pp. 432-436).

For analysis of highly pure compositions of allosteric hemoglobin modifiers however, none of the prior art techniques can be used because the limit of detection is not low enough. The improved processes of the instant invention produce compositions of allosteric hemoglobin modifiers having very low levels of impurities (≦100 ppm (0.0100% w/w) of PEM in efaproxiral-Na). Consequently, there remains a need for a method for analyzing these compounds which has a low detection limit and good specificity to measure very low levels of PEM, as well as other polymeric impurities with adequate sensitivity. Since pyrolysis/gas chromatography/mass spectrometry (PY/GC/MS) has been used for identification of polymers in relatively intractable matrices, it was evaluated to determine whether it would be useful for trace level analysis of polymers in efaproxiral-Na. Extensive development led to the discovery of a method for quantitation of trace levels of PEM (limit of quantitation=10 ppm). The PY/GC/MS method described herein is a novel analytical technique that utilizes single ion monitoring and an isotopically labeled PEM internal standard to provide the sensitivity, precision, accuracy and reproducibility required for the detection and quantitation of a trace level impurity. This technique can be extended to the analysis of compositions of allosteric hemoglobin modifiers containing polymeric impurities other than PEM in the event that the method of synthesis illustrated in FIG. 3 is modified.

It is therefore an object of this invention to provide compositions of allosteric hemoglobin modifying compounds having lower amounts of polymeric impurities, particularly PEM, as well as, lower amounts of impurities in general.

It is also an objective of the present invention to provide improved methods for the synthesis of compositions of allosteric hemoglobin modifying compounds having lower amounts of polymeric impurities.

It is another object of the present invention to provide improved methods for purification of compositions of allosteric hemoglobin modifying compounds prepared by any known synthetic method, in particular by the method disclosed herein.

Finally, it is an objective of the present invention to provide a method for analyzing compositions of allosteric hemoglobin modifying compounds, which enables detection and quantification of low levels of impurities, particularly polymeric impurities.

SUMMARY OF THE INVENTION

The present invention includes novel compositions of allosteric hemoglobin modifier compounds that are substantially free of impurities, particularly polymeric impurities. The compositions of allosteric hemoglobin modifier compounds included within the scope of this invention are generally represented by the following formula:

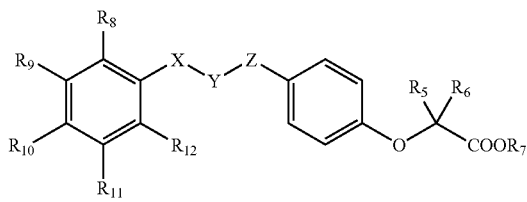

wherein

X and Z are independently selected from the group consisting of $CH_2$, CO, NH or O, and Y is selected from the group consisting of CO or NH, with the caveat that X, Y, and Z must all be different from each other;

$R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups, or alkyl moieties of part of an aliphatic ring connecting $R_5$ and $R_6$;

$R_7$ is a selected from the group consisting of hydrogen, a cationic counterion, selected from the group including, but not limited to sodium, potassium or ammonium, a metal, or a substituted or unsubstituted $C_{1-6}$ alkyl group; and $R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

In a preferred embodiment of the invention, the allosteric hemoglobin modifying compounds are generally represented by the following formula:

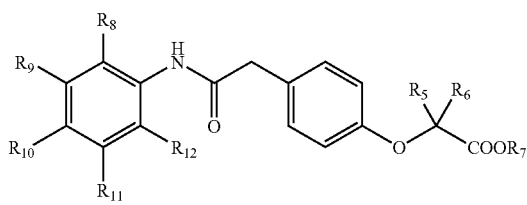

wherein $R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups or alkyl moieties of part of an aliphatic ring connecting $R_5$ and $R_6$;

$R_7$ is a selected from the group consisting of hydrogen, a cationic counterion, including but not limited to sodium, potassium or ammonium, a metal, or a substituted or unsubstituted $C_{1-6}$ alkyl group; and $R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

More preferably $R_5$ and $R_6$ are independently selected from H or $CH_3$ and $R_7$ is selected from hydrogen or a cationic counterion as defined above.

In the most preferred embodiment of the invention the allosteric hemoglobin modifier compound is 2-[4-((((3,5-dimethylphenyl)amino)carbonyl)methyl)phenoxy]-2-methyl propionic acid (efaproxiral) (5).

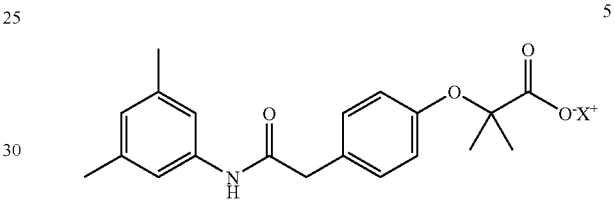

An impurity includes any substance that does not belong in the allosteric hemoglobin modifier composition. Typically, the impurities present in the compositions are a result of the process employed to produce the allosteric hemoglobin modifier compound. For example, polymeric impurities are produced by the polymerization of one of the starting materials used to synthesize these compounds via the method exemplified by Process B. In a preferred embodiment of the invention the allosteric hemoglobin modifier composition is the sodium salt of efaproxiral (5) containing less than 0.010% non-polymeric impurities and less than 100 ppm (0.01%) of polymeric impurities, and more specifically the polymeric impurity PEM. In a most preferred embodiment, the allosteric hemoglobin modifier composition contains less than 80 ppm (0.008%) of polymeric impurities, specifically the polymeric impurity PEM.

The present invention includes methods for the preparation of compositions of allosteric hemoglobin modifier compounds that are substantially free of polymeric impurities. The improved method for preparing allosteric hemoglobin modifier compounds is shown in FIG. 3, which illustrates the synthesis of efaproxiral sodium (5) as an exemplary compound. In the most preferred embodiment of the invention, the allosteric hemoglobin modifier compounds are synthesized in reaction vessels that do not contain metals that promote the formation of polymeric byproducts and the crude synthetic products produced are then purified by extraction with methyl isobutyl ketone (MIBK) followed by an ethanol/acetone recrystallization. In this embodiment of the invention, the method for preparing compositions of allosteric hemoglobin modifier compounds is comprised of the steps of a) coupling a substituted aniline with 4-hydroxyphenylacetic acid to yield the corresponding substituted phenol; b) adding the product of step (a) to an alkyl ester halide to yield a substituted ester; and c) saponifying the substituted ester to provide the salt of the acid. As noted above, in a preferred embodiment all steps are performed in a reaction vessel that does not contain metals (referred to herein as "catalytic metals") that promote the formation of polymeric byproducts. Examples of catalytic metals that promote the formation of polymeric byproducts include, but are not limited to copper, iron, nickel, palladium and rhodium. Acceptable materials for reaction vessels include, but are not limited to glass lined stainless steel, passivated stainless steel, Hastelloy® or similar alloys low in available catalytic metals.

The present invention also includes improved methods for purifying crude synthetic compositions of allosteric hemoglobin modifier compositions containing impurities, particularly polymeric impurities. The improved methods for purifying these compositions include, but are not limited to extracting the crude compositions obtained following step (c) with any water immiscible or partially immiscible solvent in which the ester formed in step (c) is soluble, including, but not limited to methyl isobutyl ketone (MIBK), isopropyl acetate, ethyl acetate, methyl ethyl ketone, chlorinated solvents selected from the group including, but not limited to chloroform and methylene chloride and recrystallizing the crude compositions with solvents including, but not limited to ethanol, acetone and mixtures of acetone/ethanol, acetone/methanol and ethanol/methanol/acetone/water. In a preferred embodiment, the recyrstallized product is further purified by filtering through a polymeric filter, wherein said polymeric filter is selected from the group including, but not limited to poly(vinylidene difluoride) (PVDF) or a cellulose ester filter.

Finally the present invention includes a method for analyzing compositions of allosteric hemoglobin modifying compounds for impurities, particularly polymeric impurities and more particularly PEM. In this embodiment of the invention, the method for analyzing compositions of allosteric hemoglobin modifier compounds is comprised of the steps of a) pyrolyzing (PY) a composition comprised of an allosteric hemoglobin modifier compound and b) analyzing said pyrolyzed composition by gas chromatography/mass spectrometry (GC/MS). In order to improve the sensitivity of the method by the two orders of magnitude needed to measure trace amounts of polymeric impurity an isotopic internal standard is added to the sample prior to analysis. It is believed that this is the first report of the use of an internal standard, particularly an isotopic internal standard prior to analysis by PY/GC/MS for trace level analysis of polymers in drugs. The internal standard is added in an amount so as to produce a concentration approximately the same as that expected for the polymeric impurity in the compound being analyzed, which in the instant application is endogenous PEM. As noted above, the use of an internal standard, particularly an isotopic internal standard greatly improves the sensitivity while maintaining precision and accuracy in the analytical method making quantitative measurements in the 10-100 ppm range possible. Isotopes of any atom can be used including, but not limited to isotopes of hydrogen, carbon, oxygen and nitrogen. Examples of such isotopes include, but are not limited to deuterium (D), carbon 13 ($^{13}C$), oxygen 18 ($^{18}O$) and nitrogen ($^{15}N$). The method described herein can be extended to the identification and quantification of any compound amenable to analysis by PY/GC/MS.

Additional advantages and novel features of this invention shall be set forth in part in the description and examples that follow, and in part will become apparent to those skilled in the art upon examination of the following or may be learned by the practice of the invention. The advantages of the invention may be realized and attained by means of the instrumentation and in combinations particularly pointed out in the appended claims. It is to be understood that both the foregoing general description and the following detailed description are exemplary and explanatory only and are not restrictive of the invention as claimed.

DETAILED DESCRIPTION OF THE PREFERRED EMBODIMENT

Figure 1A:
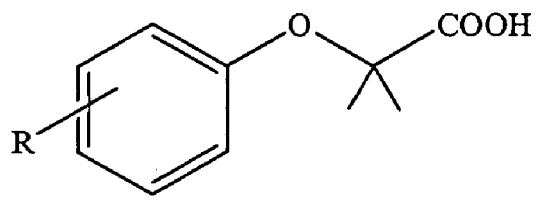
FIGS. 1A-1E depict the chemical structures of a variety of compounds that have a "right-shifting" allosteric effect on hemoglobin. The family of compounds illustrated by FIG. 1D (referred to as RSR compounds) are representative of a large family of compounds having a strong allosteric effect.
Figure 1B:
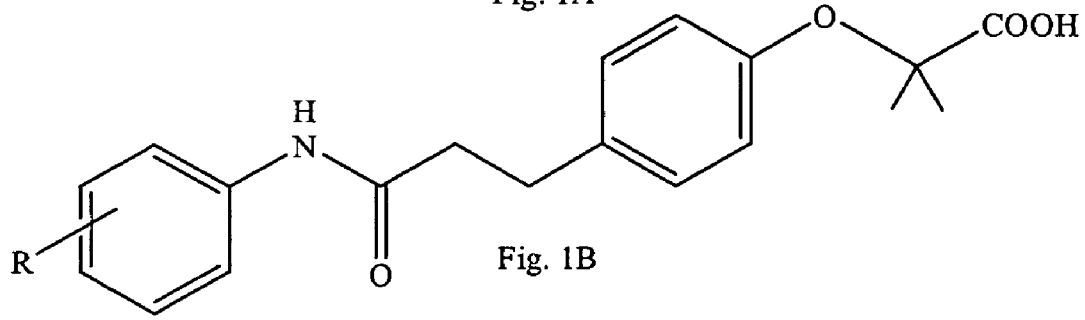
Figure 1C:
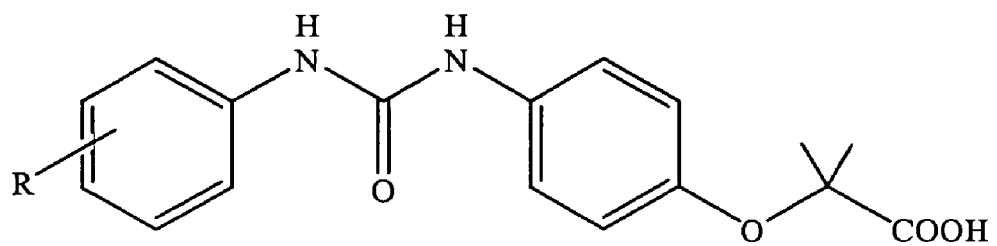
Figure 1D:
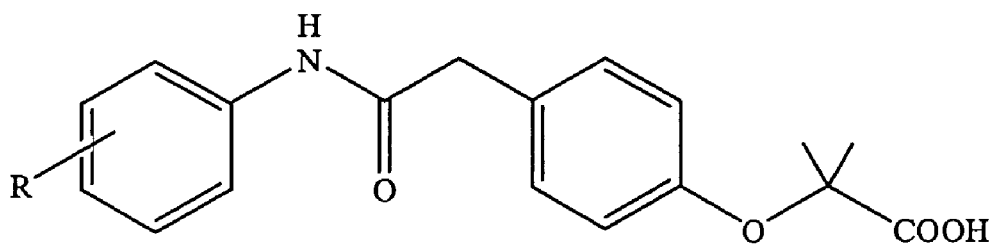
Figure 1E:
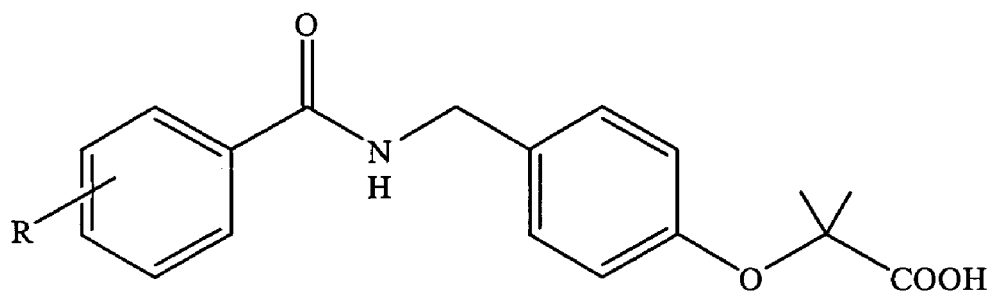
Figure 2:
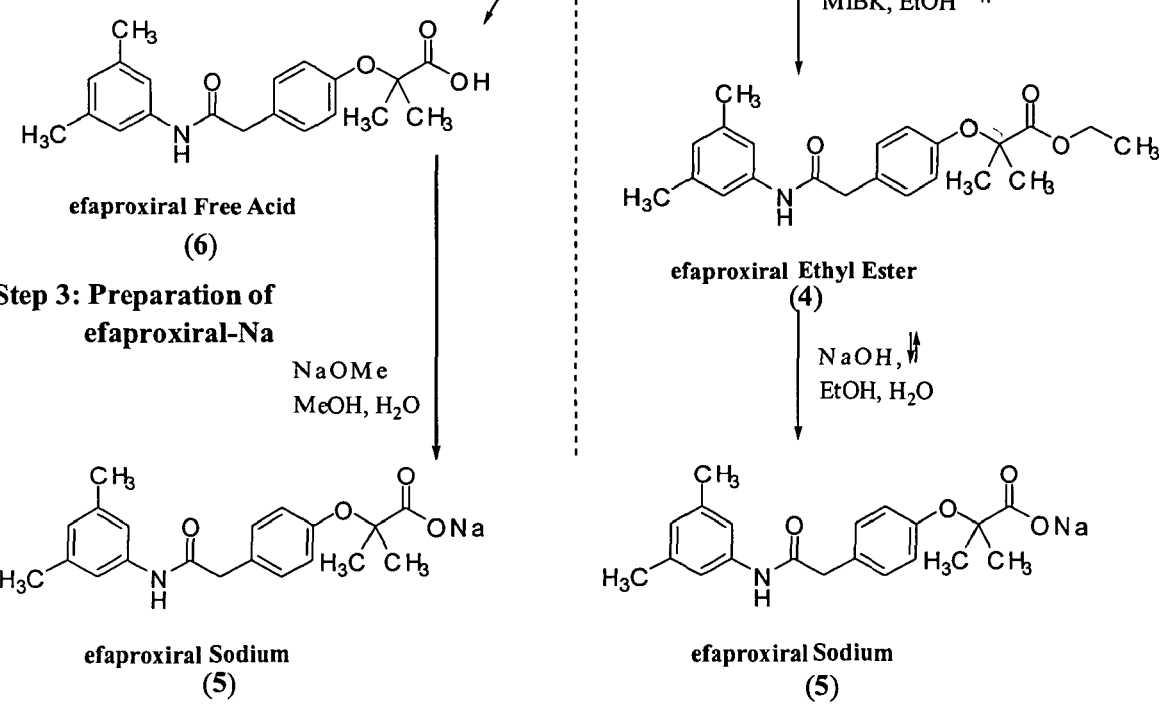
FIG. 2 illustrates two of the principal prior art methods developed for the synthesis of the allosteric hemoglobin modifier 2-[4-((((3,5-dimethylphenyl)amino)carbonyl)methyl) phenoxy]-2-methyl propionic acid (also known as efaproxiral).

The present invention includes novel compositions of allosteric hemoglobin modifier compounds that are substantially free of impurities, particularly polymeric impurities. In one embodiment, the allosteric hemoglobin modifier composition is 2-[4-((((3,5-dimethylphenyl)amino)carbonyl)methyl)phenoxy]-2-methyl propionic acid (also known as efaproxiral) containing less than 100 ppm of the polymeric impurity poly(ethyl methacrylate) (PEM). The present invention includes methods for the preparation of compositions of allosteric hemoglobin modifier compounds having very low levels of impurities. In one embodiment, the method of the invention is comprised of synthesizing the allosteric hemoglobin modifier compound according to the method described herein using a reaction vessel that does not contain available metals that promote the formation of polymeric byproducts, referred to herein as "catalytic metals."

The present invention also includes improved methods for purifying crude synthetic compositions of allosteric hemoglobin modifier compositions containing impurities, particularly polymeric impurities. The improved methods for purifying these compositions include, but are not limited to extracting the crude compositions with any water immiscible or partially immiscible solvent in which the polymeric impurity is soluble, including but not limited to methyl isobutyl ketone (MIBK), isopropyl acetate, ethyl acetate, methyl ethyl ketone, and chlorinated solvents selected from the group including, but not limited to chloroform and methylene chloride and recrystallizing the crude compositions with solvents selected from the group including, but not limited to ethanol, acetone and mixtures of acetone/ethanol, acetone/methanol and ethanol/methanol/acetone/water. In a preferred embodiment, a solution of the recyrstallized product is further purified by filtering through a polymeric filter, wherein said polymeric filter is selected from the group including, but not limited to poly(vinylidene difluoride) (PVDF) or a cellulose ester filter.

Finally, the present invention includes a method for analyzing compositions of allosteric hemoglobin modifying compounds for impurities, particularly PEM. In this embodiment of the invention, the method for analyzing compositions of allosteric hemoglobin modifier compounds is comprised of the steps of a) pyrolyzing a composition comprised of an allosteric hemoglobin modifier compound and b) analyzing said pyrolyzed composition by gas chromatography/mass spectrometry (GC/MS) employing an internal standard, particularly an isotopically labeled version of the polymeric analyte as the internal standard or an analog of the polymeric analyte as the internal standard.

Various terms are used herein to refer to aspects of the present invention. To aid in the clarification of the description of the components of this invention, the following definitions are provided.

It is to be noted that the term "a" or "an" entity refers to one or more of that entity; for example, an allosteric hemoglobin modifying compound refers to one or more allosteric hemoglobin modifying compounds. As such, the terms "a" or "an," "one or more" and "at least one," are used interchangeably herein.

As used herein the term "allosteric hemoglobin modifier compounds" or "allosteric effector compounds" refers to a specific class of compounds, which can be generally represented by the following formula:

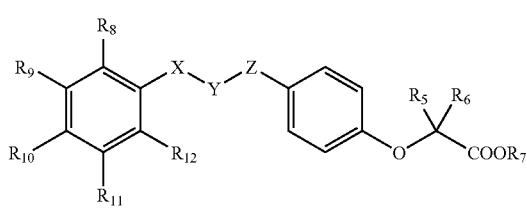

wherein

X and Z are independently selected from the group consisting of $CH_2$, CO, NH or O, and Y is selected from the group consisting of CO or NH, with the caveat that X, Y, and Z must all be different from each other;

$R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups, or alkyl moieties of part of an aliphatic ring connecting $R_5$ and $R_6$;

$R_7$ is a selected from the group consisting of hydrogen, a cationic counterion, selected from the group including but not limited to sodium, potassium or ammonium, a metal, or a substituted or unsubstituted $C_{1-6}$ alkyl group; and $R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

In a preferred embodiment of the invention, the allosteric hemoglobin modifying compounds are generally represented by the following formula:

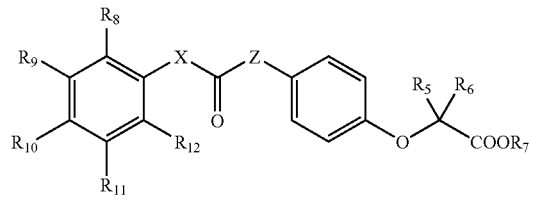

wherein

X and Z are independently selected from the group consisting of $CH_2$, NH or O;

$R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups, or alkyl moieties of part of an aliphatic ring connecting $R_5$ and $R_6$;

$R_7$ is a selected from the group consisting of hydrogen, a cationic counterion, including but not limited to sodium, potassium or ammonium, a metal, or a substituted or unsubstituted $C_{1-6}$ alkyl group; and $R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

In another preferred embodiment of the invention, the allosteric hemoglobin modifying compounds are generally represented by the following formula:

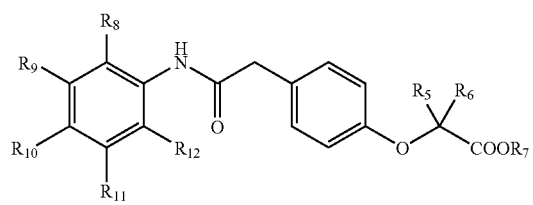

wherein $R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups or alkyl moieties of part of an aliphatic ring connecting $R_5$ and $R_6$;

$R_7$ is a selected from the group consisting of hydrogen, a cationic counterion, including but not limited to sodium, potassium or ammonium, a metal, or a substituted or unsubstituted $C_{1-6}$ alkyl group; and $R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

More preferably $R_5$ and $R_6$ are independently selected from H or $CH_3$ and $R_7$ is selected from hydrogen or a cationic counterion as defined above.

In the most preferred embodiment the allosteric hemoglobin modifier compound is 2-[4-((((3,5-dimethylphenyl) amino)carbonyl)methyl)phenoxy]-2-methyl propionic acid (efaproxiral) (5).

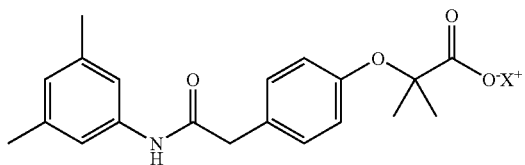

5

As used herein the term "impurity" includes any substance that does not belong in the allosteric hemoglobin modifier composition, typically resulting from the synthesis of the allosteric hemoglobin modifier or from products of its degradation. The term impurity includes, but is not limited to polymeric impurities, such as poly(ethyl methacrylate) and precursors to this compound, which are referred to herein collectively as PEM, as well as other related impurities resulting from the synthetic process.

As used herein the term "polymeric impurity" refers to any polymerized byproduct of the process employed to produce an allosteric hemoglobin modifier compound. In one embodiment, the polymeric impurity is selected from a compound having the following structure:

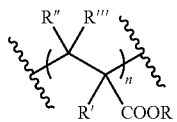

wherein
R, R', R" and R'" are independently selected from the group consisting of a substituted or unsubstituted $C_{1-12}$ alkyl group and hydrogen; and
n is any number of units appropriate for a polymer of repeating units.

A polymeric impurity produced as a result of the synthesis of compound (5) as described herein is poly(ethyl methacrylate) (PEM).

Synthesis of the allosteric hemoglobin modifiers of the invention can result in polymeric byproducts of up to approximately 10% by weight depending upon reaction conditions. As noted above, in the synthesis of efaproxiral sodium (5) via Process B, the polymeric impurity PEM is typically formed in concentrations of from approximately 0.5% (5000 ppm) to 9% (90,000 ppm) by weight.

"Related impurities" refer to all nonpolymeric impurities resulting from the synthetic process such as structural isomers or decomposition products. Related impurities include but are not limited to 3-monomethyl efaproxiral (3MMRS13), α-desmethyl efaproxiral (DDMRS13), monomethyl α to COOH (DMRS13), 3,4-dimethyl efaproxiral (3,4DMRS13), α ethyl efaproxiral, diacid (DA), 3,5-dimethyl aniline, amidophenol and the ethyl esters of the related impurities having the structures described in Table 1. Other related impurities would be obvious to one of skill in the art. With respect to the related impurities, the purification method described herein either meets or exceeds the acceptable levels of impurities for a high dose parenteral drug set forth in the International Conference on Harmonisation (ICH) Guidelines, which are published in the Federal Register or by the EMEA. For high dose drugs the limit for any unqualified impurity is NMT 0.05%. In a preferred embodiment of the invention, the related impurities are collectively present in an amount not exceeding about 0.75% (75000 ppm) by weight.

By "substantially free" of impurities it is meant a degree of polymeric impurity not exceeding about 0.5% (5000 ppm) by weight, more preferably a degree of polymeric impurity not exceeding 0.1%, 0.07%, 0.05%, 0.025%, 0.02%, 0.015%, 0.01% (100 ppm), 0.009%, and most preferably an amount of polymeric impurity not exceeding 0.008% (80 ppm), 0.007% or 0.006% (60 ppm) by weight or less, including 0.005% (50 ppm), 0.004% (40 ppm), 0.003% (30 ppm) and 0.001% (10 ppm) and a degree of related impurities not exceeding about 0.1% by weight, more preferably a degree of related impurity not exceeding 0.09%, 0.08%, 0.07%, 0.06% or 0.05%.

As would be known to one of skill in the art a composition which is 97% substantially free of impurities would also be considered to be 97% substantially pure, etc.

As used herein the term "catalyst" refers to a substance that initiates or accelerates the rate of a chemical reaction without being consumed in the reaction. Typically, a catalyst lowers the activation energy for a chemical reaction by providing an alternate pathway for the reaction. Catalysts that promote the formation of polymerized byproducts include, but are not limited to metals such as copper, iron, nickel, palladium and rhodium. The metals that promote the formation of polymeric byproducts are referred to herein as "catalytic metals."

As used herein the term "extraction" or "extracting" refers to a liquid-liquid partition or the process of transferring a dissolved substance from one liquid phase to another (immiscible or partially miscible) liquid phase in contact with it.

As used herein the term "recrystallization" or "recrystallizing" is a standard term which refers to a means for purifying materials by precipitation from a solvent(s).

Note, that throughout this application various citations are provided. Each citation is specifically incorporated herein in its entirety by reference.

The present invention includes novel compositions of allosteric hemoglobin modifier compounds that are substantially free of impurities, particularly polymeric impurities. The compositions of allosteric hemoglobin modifier compounds included within the scope of this invention are illustrated by the general structure set forth above. As noted above, an impurity includes any substance that is not the desired allosteric hemoglobin modifier composition. Typically, the impurities present in the compositions are a result of the process employed to produce the allosteric hemoglobin modifier compound. For example, the polymeric impurities are produced by the polymerization of one of the starting materials used to synthesize these compounds via the method exemplified by Process B. In a preferred embodiment of the invention the allosteric hemoglobin modifier composition is the sodium salt of efaproxiral (5) containing less than 100 ppm (0.01%) of polymeric impurities, specifically the polymeric impurity PEM and less than 1000 ppm (0.1%) of any related impurity. In a most preferred embodiment, the allosteric hemoglobin modifier composition contains less than 80 ppm of polymeric impurities and less than 500 ppm of any related impurity.

The present invention includes methods for the preparation of compositions of allosteric hemoglobin modifier compounds that are substantially free of impurities. By "substantially free" of impurities it is meant a degree of polymeric impurity not exceeding about 0.5% (5000 ppm) by weight, more preferably a degree of polymeric impurity not exceeding 0.1%, 0.07%, 0.05%, 0.025%, 0.02%, 0.015%, 0.01% (100 ppm), 0.009%, and most preferably an amount of polymeric impurity not exceeding 0.008% (80 ppm), 0.007% or 0.006% (60 ppm) by weight or less, including 0.005% (50 ppm), 0.004% (40 ppm), 0.003% (30 ppm), and 0.001% (10 ppm) and a degree of related impurities not exceeding about 0.1% by weight, more preferably a degree of related impurity not exceeding 0.09%, 0.08%, 0.07%, 0.06% or 0.05%. In this embodiment of the invention the method for preparing compositions of allosteric hemoglobin modifier compounds is comprised of the steps of a) coupling a substituted aniline with 4-hydroxyphenylacetic acid to yield the corresponding substituted phenol; b) adding the product of step (a) to an alkyl ester halide to yield a substituted ester; and c) saponifying the substituted ester to provide the salt of the acid, wherein all steps are performed in a reaction vessel that does not contain metals that promote the formation of polymeric byproducts, referred to herein as catalytic metals. Examples of catalytic metals include, but are not limited to copper, iron, nickel, palladium and rhodium. Stainless steel (SS) is generally comprised of predominantly nickel, chromium and molybdenum. Acceptable materials for reaction vessels include, but are not limited to glass lined stainless steel, passivated stainless steel, Hastelloy® or similar alloys. The Hastelloy 276® alloy is comprised of predominantly nickel, chromium and molybdenum.

Example 1 describes the synthesis of the sodium salt of efaproxiral (efaproxiral-Na) (5) according to the method of this invention using either a Hastelloy or SS reaction vessel. The synthesis of efaproxiral-Na (5) can be performed in any reaction vessel that does not promote the formation of the polymeric impurity PEM, including but not limited to an SS (316) reactor, a Hastelloy 276® reactor or a glass-lined SS reactor. In a preferred embodiment, the synthesis of (5) is performed in a Hastelloy 276®, SS or glass-lined SS reactor. The product prepared by the method described in Example 1 contained less than 3% by weight of the poly(ethyl methacrylate) (PEM) impurity. The use of a Monel® reaction vessel, on the other hand, resulted in a product that contained about 9% by weight PEM. Monel® is an alloy comprised predominantly of copper and nickel. Thus, the change in reaction vessel significantly reduced the amount of PEM formed during the reaction.

The present invention also includes improved methods for purifying crude synthetic compositions of allosteric hemoglobin modifier compositions containing impurities, particularly polymeric impurities. In this embodiment of the invention, the method for preparing compositions of allosteric hemoglobin modifier compounds is comprised of the steps of a) coupling a substituted aniline with 4-hydroxyphenylacetic acid to yield the corresponding substituted phenol; b) adding the product of step (a) to an alkyl ester halide to yield a substituted alkyl ester; c) saponifying the substituted alkyl ester to provide the salt of the acid; and d) purifying the product obtained from step c) to obtain a product which is substantially free of impurities, particularly polymeric impurities, wherein all steps are performed in a reaction vessel that does not contain metals that promote the formation of polymeric byproducts. The improved methods for purifying these compositions include, but are not limited to extracting the crude compositions with any water immiscible or partially immiscible solvent in which the polymeric impurity is soluble, including but not limited to methyl isobutyl ketone (MIBK), isopropyl acetate, ethyl acetate, methyl ethyl ketone, chlorinated solvents selected from the group including, but not limited to chloroform and methylene chloride and recrystallizing the crude compositions with solvents including, but not limited to ethanol, acetone and mixtures of acetone/ethanol, acetone/methanol and ethanol/methanol/acetone/water. In a preferred embodiment, a solution of the recyrstallized product is further purified by filtering through a polymeric filter, wherein said polymeric filter is selected from the group including, but not limited to poly(vinylidene difluoride) (PVDF) or a cellulose ester filter.

Figure 3:
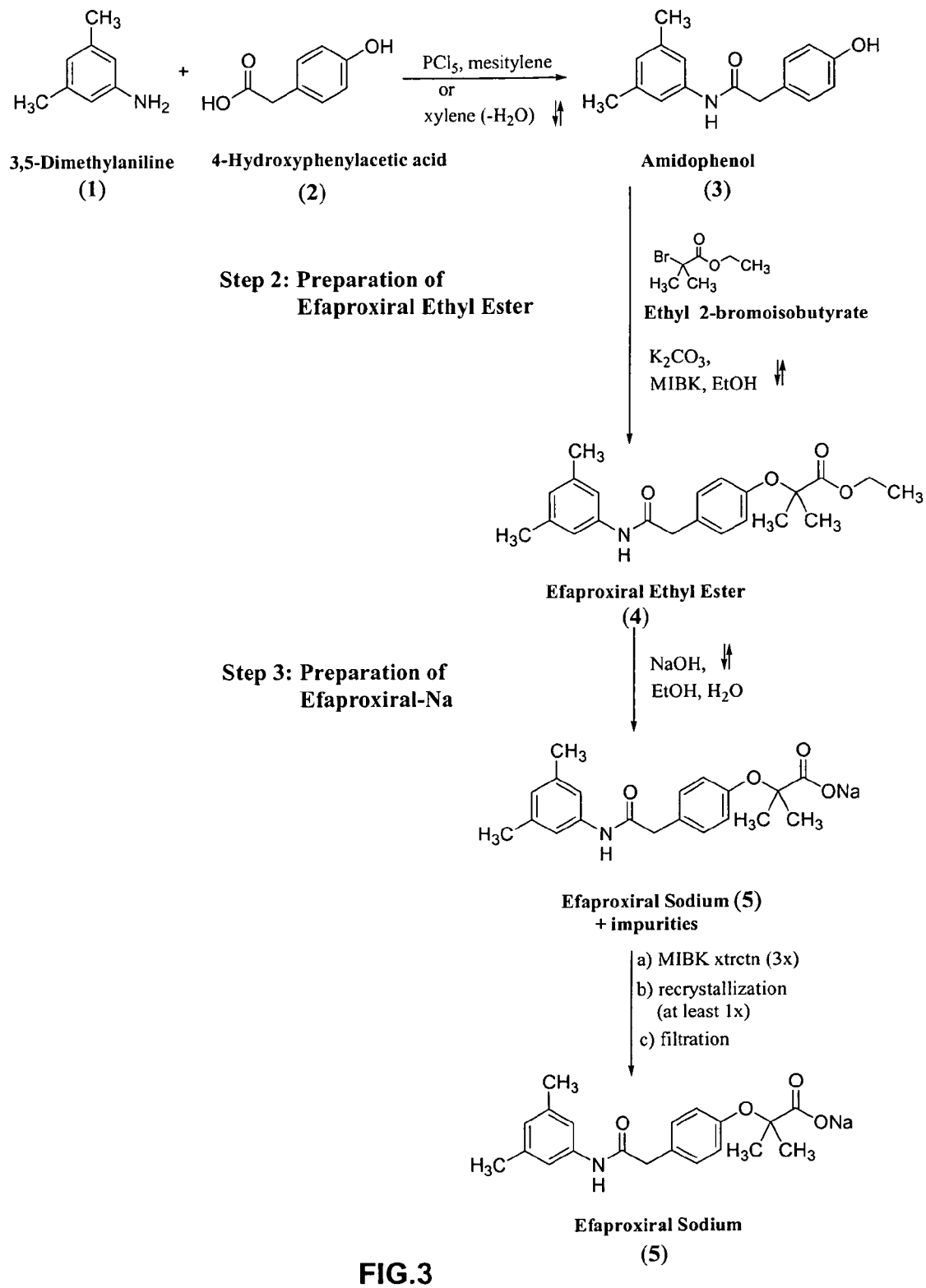
FIG. 3 depicts the improved method of the invention developed for the synthesis of the allosteric hemoglobin modifier 2-[4-((((3,5-dimethylphenyl)amino)carbonyl)methyl)phenoxy]-2-methyl propionic acid (also known as efaproxiral).

The improved methods of this invention for purifying crude synthetic compositions of allosteric hemoglobin modifier compounds are outlined in FIG. 3, using the synthesis of efaproxiral-Na (5) for purposes of illustration. Compared to prior art methods, the improved method of the invention includes addition of a purification step via extraction, a recrystallization step, a filtration step and synthesis in reaction vessels that do not contain metals that promote the formation of polymeric byproducts. Modifications were made in particular to control the levels of polymeric impurities, such as poly(ethyl methacrylate) or PEM. In one embodiment of the invention, the crude synthetic product (allosteric hemoglobin modifier compound) is extracted with a solvent such as methyl isobutyl ketone (MIBK), to remove impurities, specifically the polymeric impurity, prior to saponification. Examples of solvents that can be used to extract the crude product include any water immiscible or partially immiscible solvent in which the polymeric impurity is soluble including, but not limited to MIBK, isopropyl acetate, ethyl acetate, methyl ethyl ketone and chlorinated solvents selected from the group including, but not limited to chloroform and methylene chloride. The crude product is extracted at least one time, however in other embodiments the crude product may be extracted two or more times depending upon the impurities being removed. Exact extraction protocols can be determined without difficulty by one skilled in the art.

Example 2 describes the purification of efaproxiral-Na (5) prepared according to the method of Example 1 by extraction with methyl isobutyl ketone (MIBK).

Example 3 describes the purification of efaproxiral sodium (5) prepared according to the methods of Examples 1 and 2 by recrystallization with acetone/ethanol. The crude synthetic product, or the extracted crude synthetic product, is recrystallized using a solvent system such as ethanol, acetone and mixtures of acetone/ethanol, acetone/methanol and ethanol/methanol/acetone/water to reduce the amount of impurities, specifically polymeric impurities. Examples of solvent(s) that can be used to recrystallize these products include, but are not limited to ethanol, acetone and mixtures of acetone/ethanol, acetone/methanol and ethanol/methanol/acetone/water. The purified product contained less than 100 ppm of PEM.

In the most preferred embodiment of the invention, the allosteric hemoglobin modifier compounds are synthesized in reaction vessels that do not contain metals that promote the formation of polymeric byproducts and the crude synthetic products produced are then purified by extraction with methyl isobutyl ketone (MIBK) followed by an ethanol/acetone recrystallization.

Example 4 describes a method developed to detect and quantify trace amounts of impurities in compositions of allosteric hemoglobin compounds, specifically polymeric impurities and more specifically the polymeric impurity PEM using a GC/MS method in which the sample is pyrolyzed prior to introduction onto the GC column. (Matheson et al. (May 1997) American Laboratory, pp 24C-24F; Irwin (1982) in *Analytical Pyrolysis, A Comprehensive Guide*, Marcel Dekker, Inc.). The sample flow within the pyrolysis gas chromatography mass spectrometry (PY/GC/MS) instrument is outlined in Scheme 2 using the impurity PEM for purposes of illustration. The mass spectrometry data are collected using single ion monitoring (SIM) (Hites (1997) in *Handbook of Instrumental Techniques for Analytical Chemistry*, Settles, F. Ed., Prentice-Hall Inc. p. 620) to improve the signal to noise ratio, and selectively monitors a particular mass fragment arising from the ethyl methacrylate monomer. Using this method, levels of PEM as low as 10 ppm can reliably be quantified.

Scheme 2

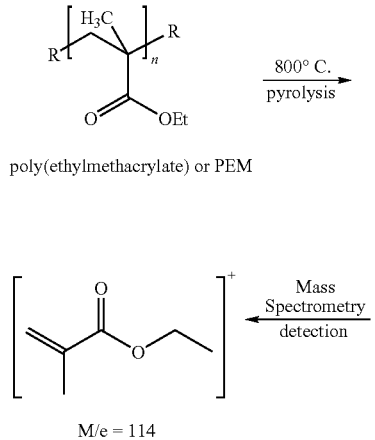

An isotopic internal standard (deuterated poly(ethyl-d5 methacrylate) (PEM-d5)) is added to the sample prior to analysis. (PEM-d5-$M_w$ 12,555, $M_n$ 12260, PI 1.02. It is believed that this is the first report of the use of an internal standard, particularly an isotopic internal standard prior to analysis by PY/GC/MS for a trace level analysis of polymers in drugs. Currently, no internal standard is used in the analysis of samples by this method. The internal standard is added in approximately the same expected concentration as the endogenous PEM. The use of an internal standard, particularly an isotopic internal standard greatly improves the precision and accuracy in the analytical method making quantitative measurements in the 10-100 ppm range possible. The increase in precision and accuracy is due to the fact that virtually the same compound, differing only in isotopic content and hence in molecular weight, is being subjected to the same pyrolysis conditions as the compound being analyzed. As noted above, the internal standard used in Example 4 was an isotope of hydrogen, namely PEM-d5, however isotopes of atoms other than hydrogen can be used including, but not limited to isotopes of carbon, oxygen and nitrogen. Examples of such isotopes include, but are not limited to deuterium (D), carbon 13 ($^{13}C$), oxygen 18 ($^{18}O$) and nitrogen ($^{15}N$). Scheme 3 depicts the monomers resulting from pyrolysis of PEM and PEM-d5 and Scheme 4 depicts the actual ions that are detected in the mass spectrometer from PEM and PEM-d5.

Scheme 3

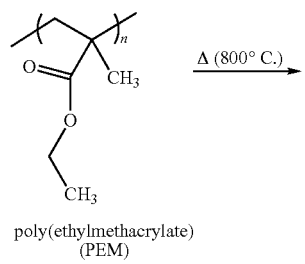

poly(ethylmethacrylate) (PEM)

-continued

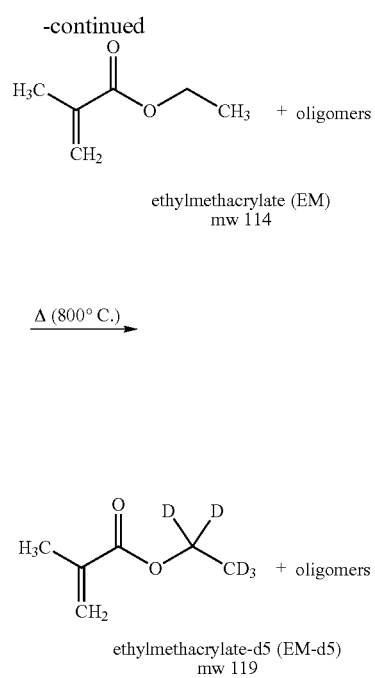

Scheme 4

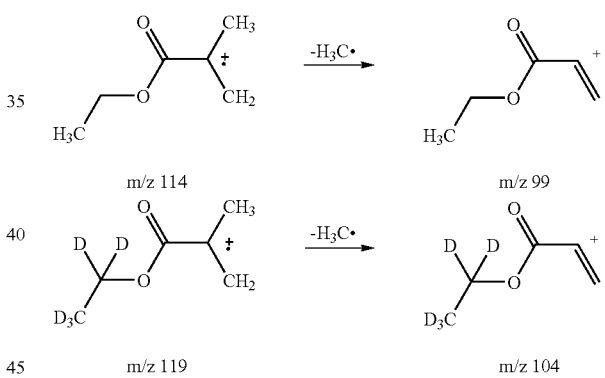

Figure 4:
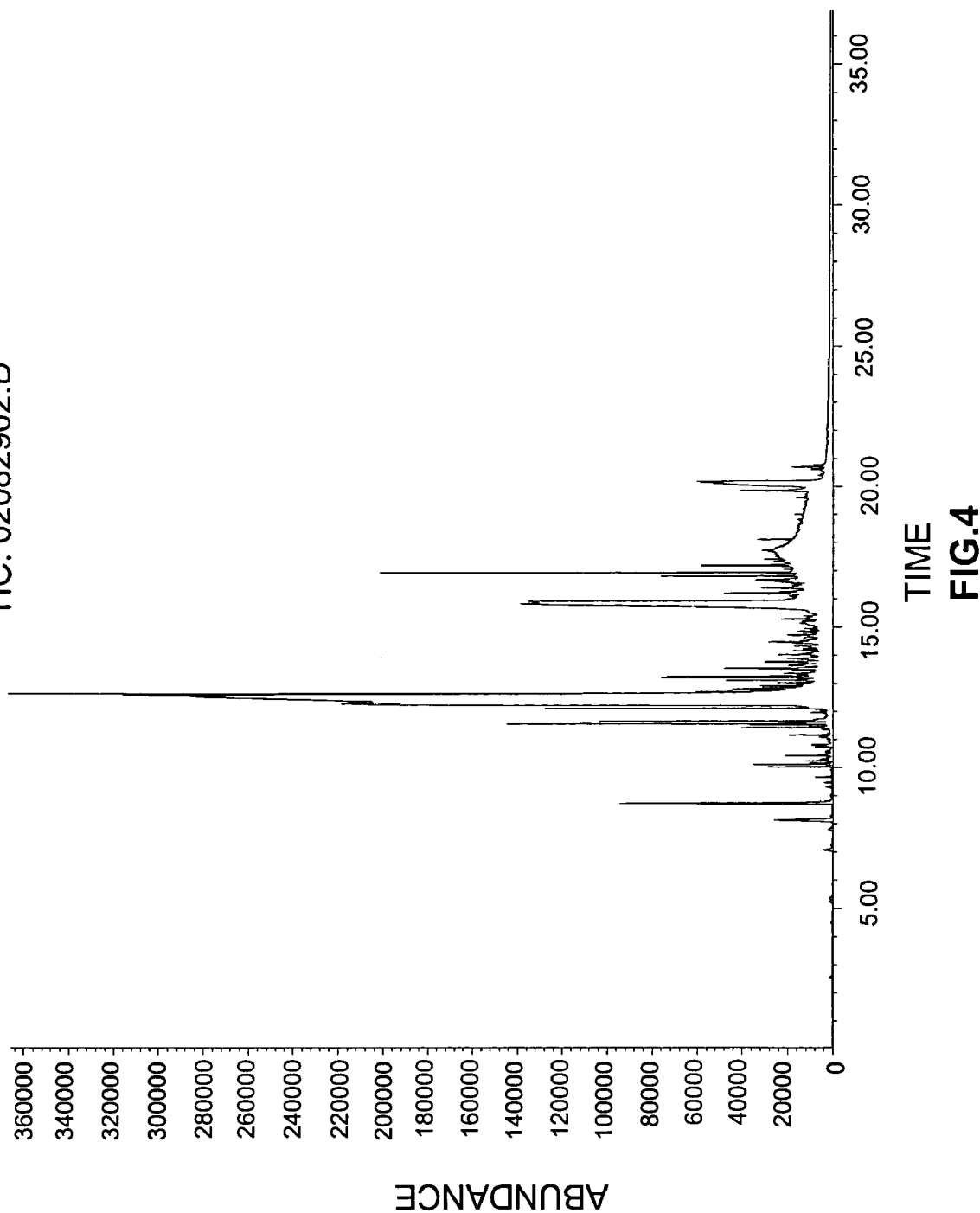
FIG. 4 depicts a total ion chromatograph (TIC) for a sample of efaproxiral, showing all of the ions resulting from pyrolysis and ionization of the drug. Additionally, the sample contains low levels of PEM (less than 50 ppm) and PEM-d5 (internal standard).
Figure 5:
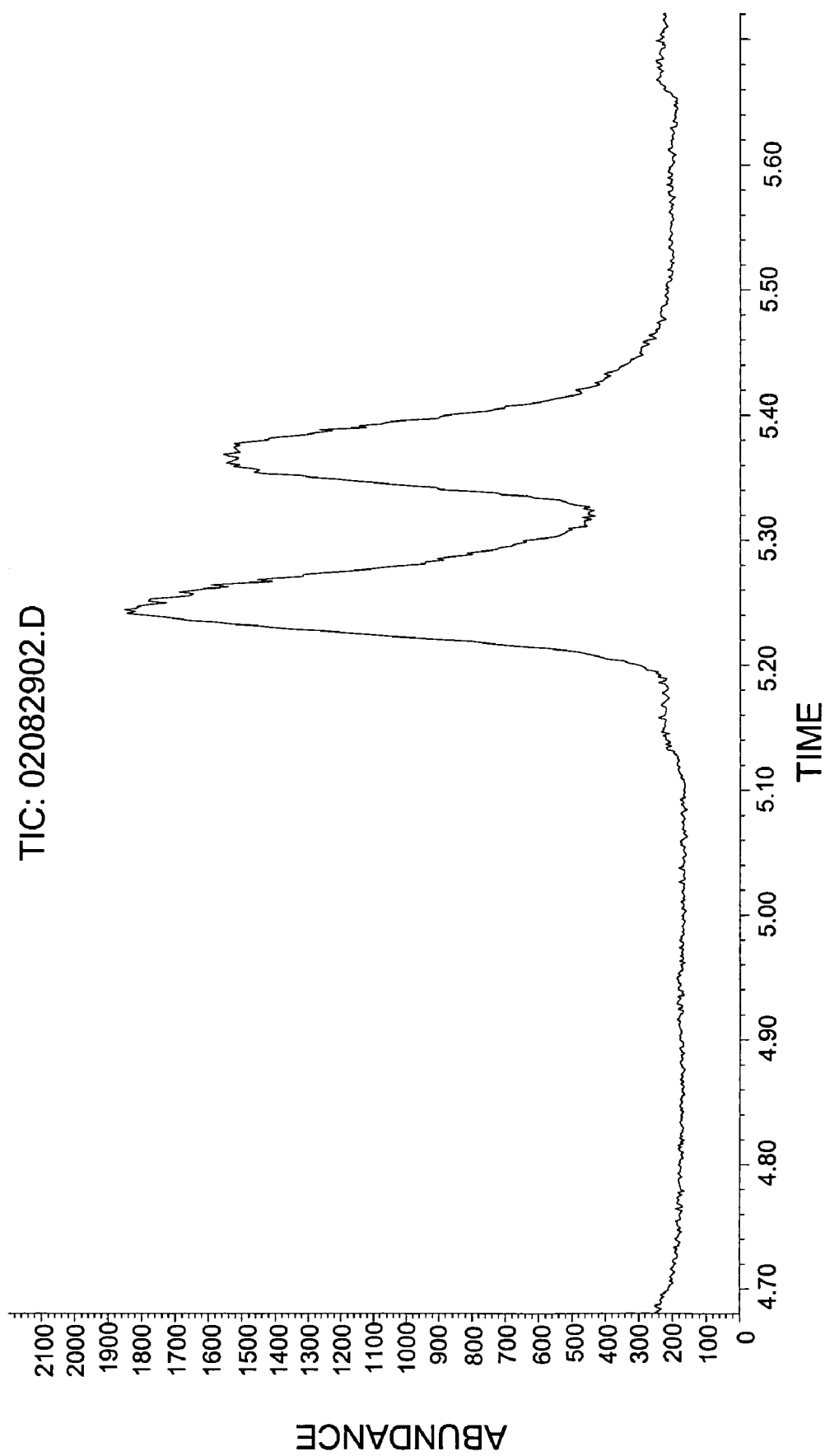
FIG. 5 depicts an expansion of the TIC of FIG. 4 in the region of 4.7 to 5.7 minutes showing the retention time of ions resulting from chromatographically separated PEM-$d_5$ (main ion: m/e 104; 5.25 minutes) and PEM (main ion: m/e 99; 5.38 minutes).
Figure 6A:
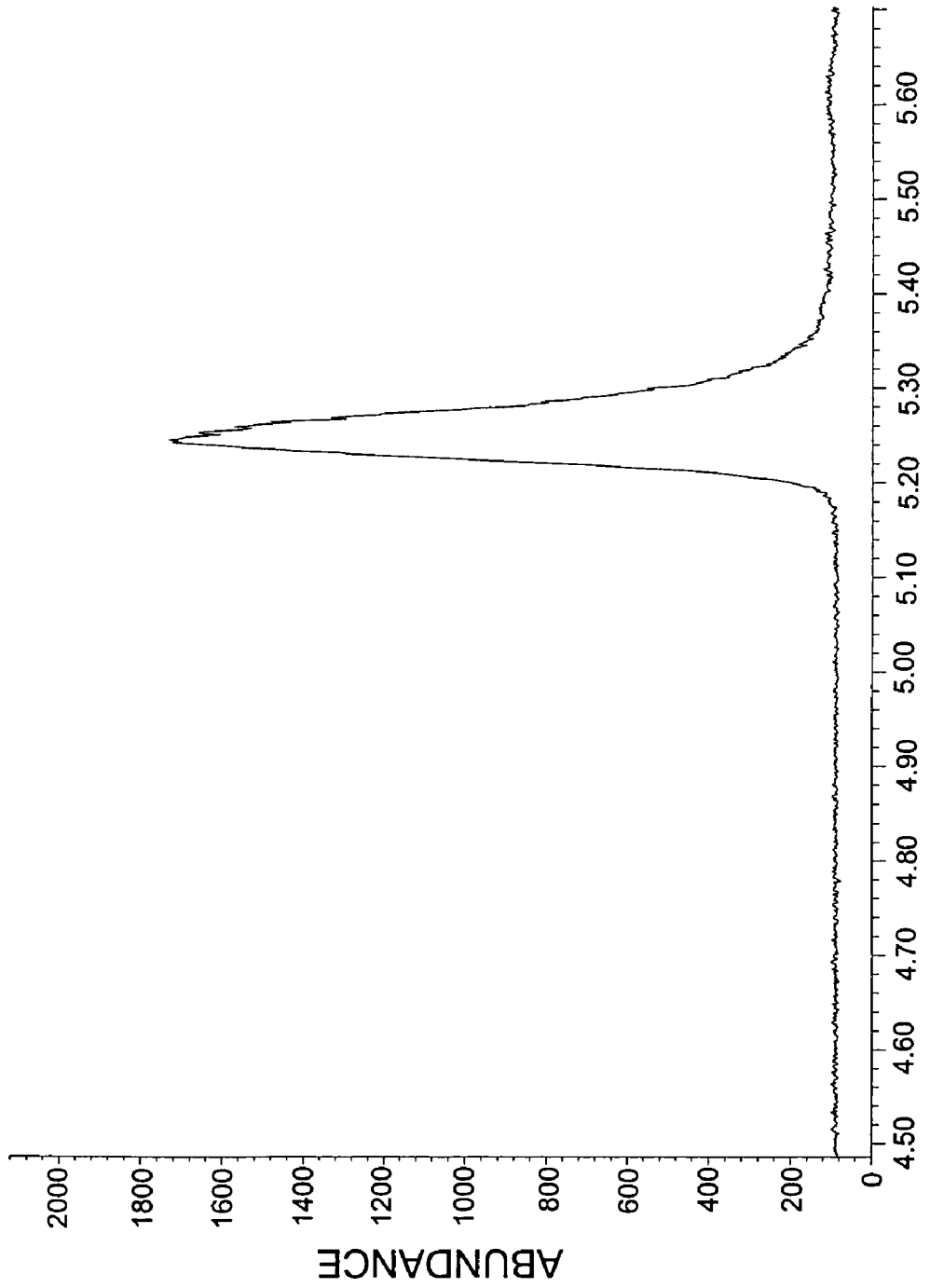
FIGS. 6A and 6B depict the chromatogram (FIG. 6A) and the mass spectra single ion monitoring (SIM) (FIG. 6B) of PEM-$d_5$ using SIM mode analysis.
Figure 6B:
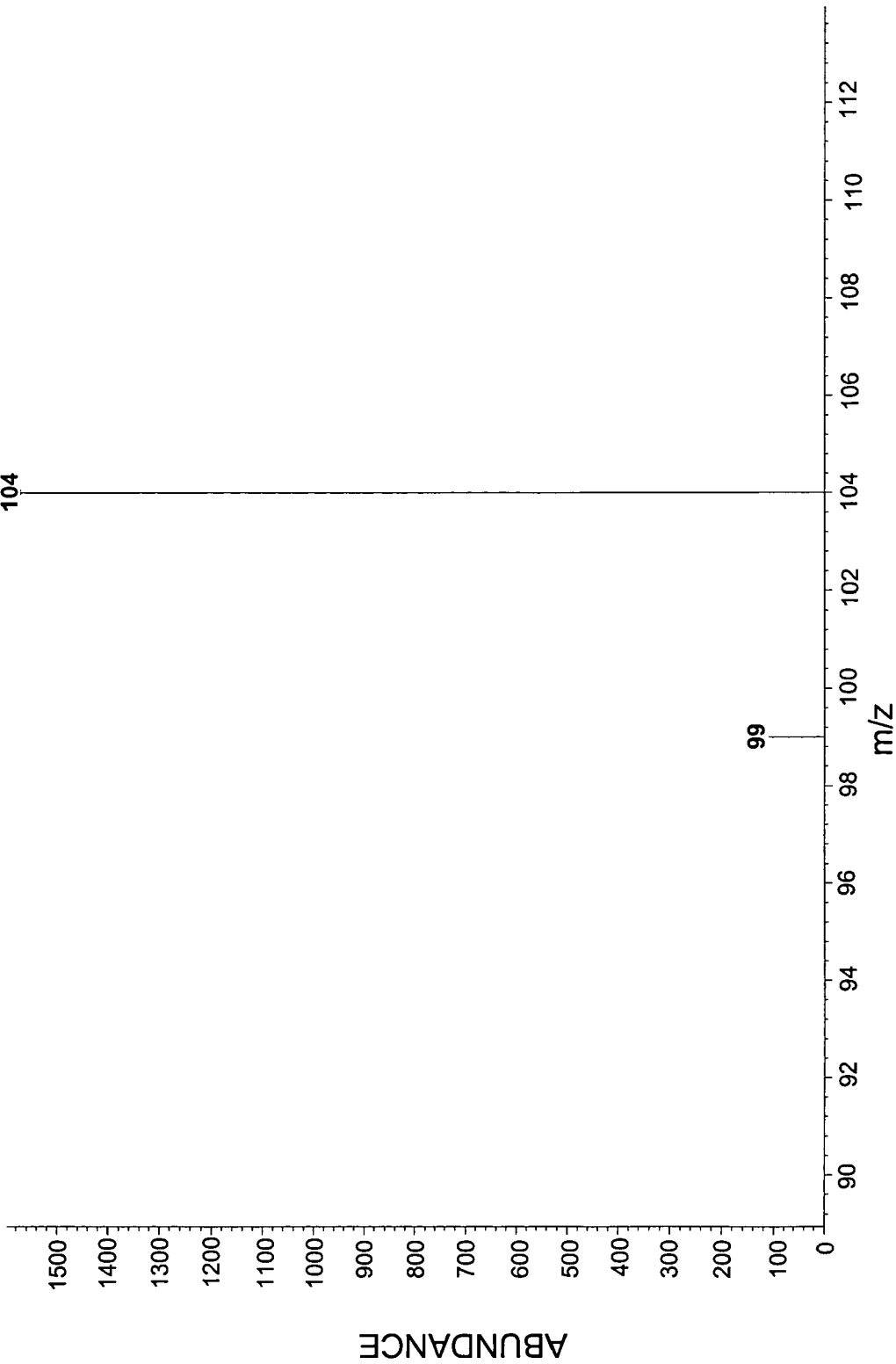
Figure 7A:
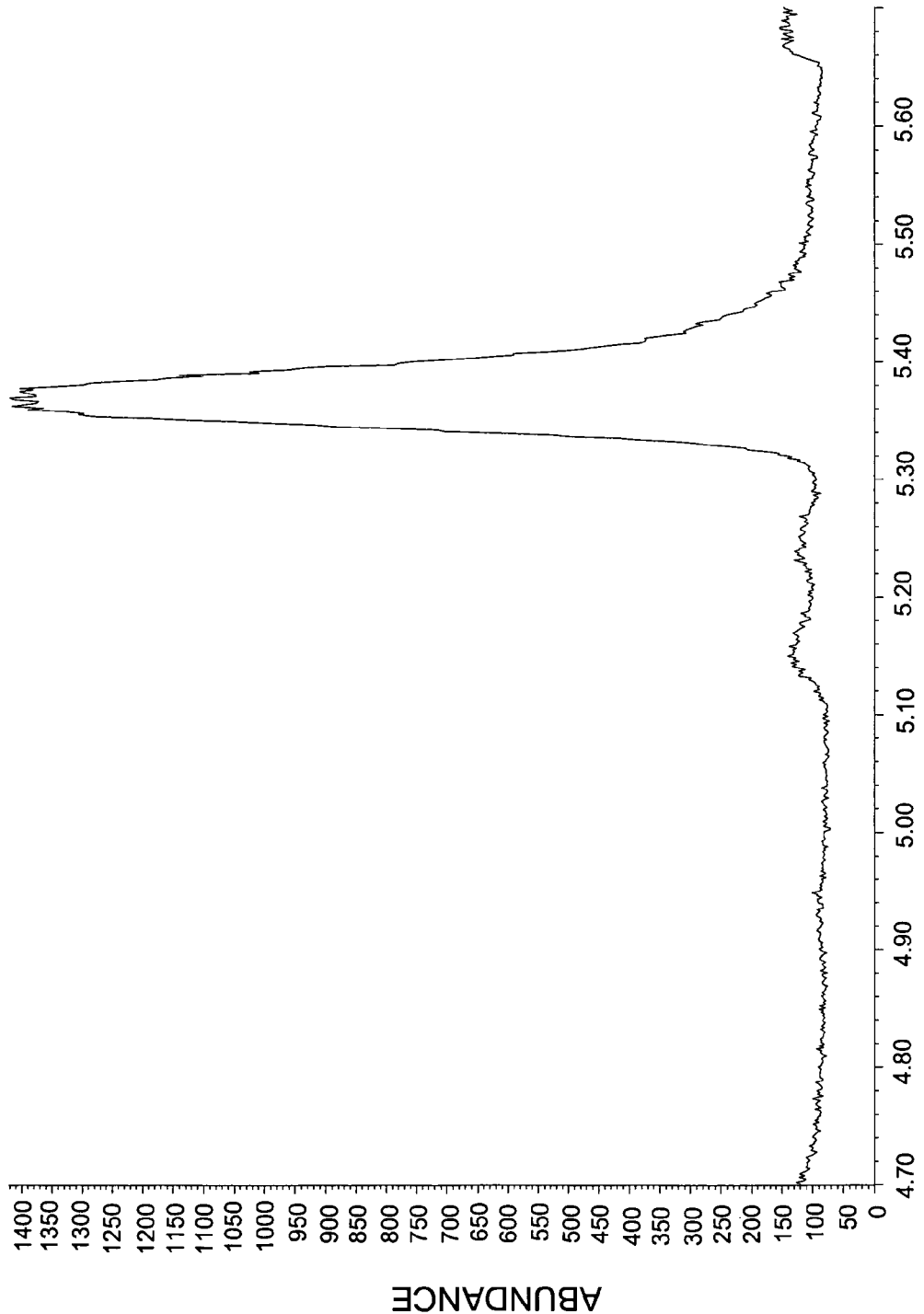
FIGS. 7A and 7B depict the chromatogram (FIG. 7A) and the mass spectra (SIM) (FIG. 7B) of PEM using SIM mode analysis.
Figure 7B:
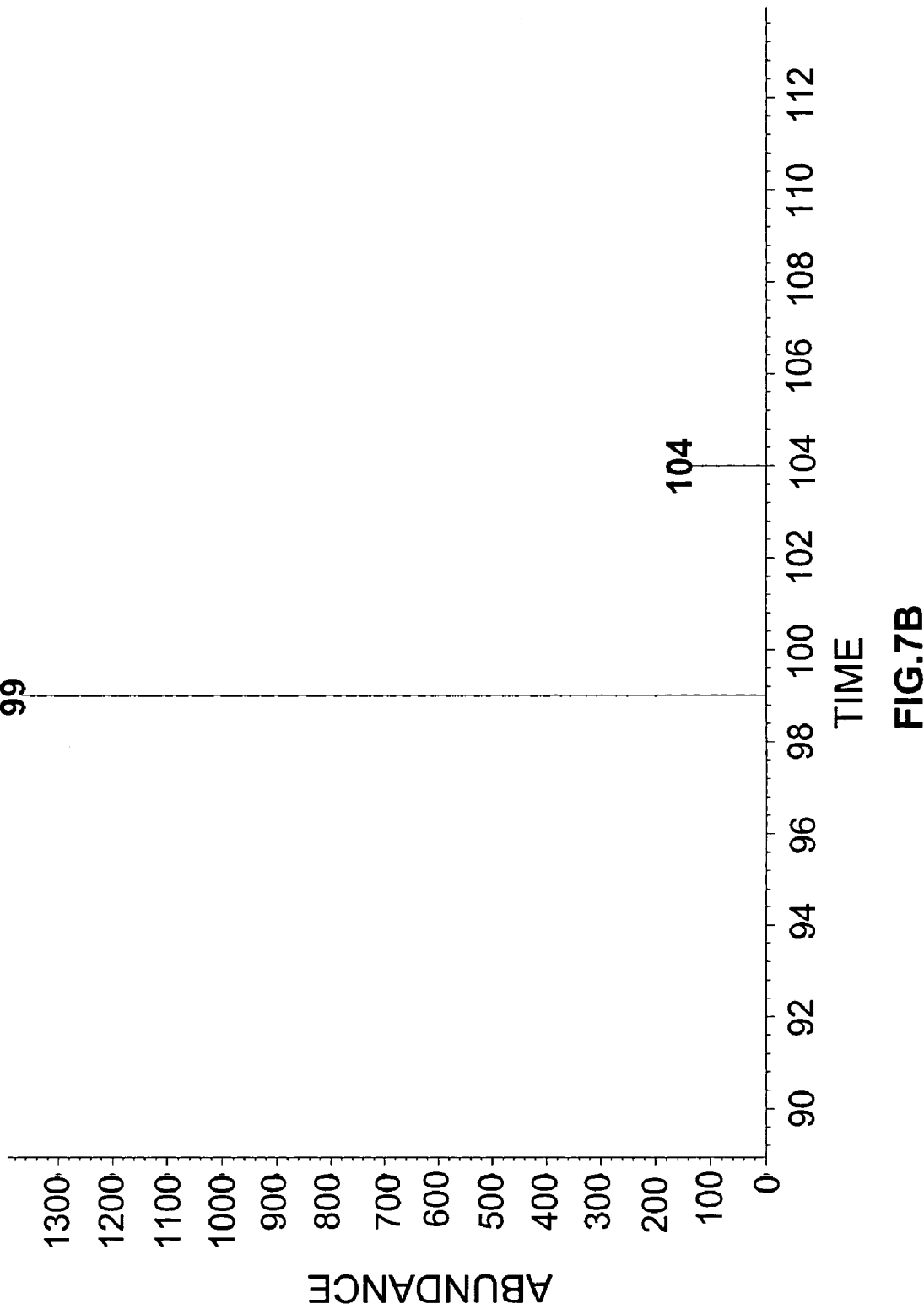

FIG. 4 depicts a total ion chromatograph (TIC) for a sample of efaproxiral, showing all of the ions resulting from pyrolysis and ionization of the drug. With reference to FIG. 4, it can be seen that the sample contains low levels of PEM (less than 50 ppm) and PEM-d5 (internal standard). FIG. 5 depicts an expansion of the TIC of FIG. 4 in the region of 4.7 to 5.7 minutes showing the retention time of ions resulting from chromatographically separated PEM-$d_5$ (main ion: m/e 104; 5.25 minutes) and PEM (main ion: m/e 99; 5.38 minutes). FIGS. 6A and 6B depict the chromatogram (FIG. 6A) and the mass spectra (SIM) (FIG. 6B) of PEM-$d_5$ using SIM mode analysis. FIGS. 7A and 7B depict the chromatogram (FIG. 7A) and the mass spectra (SIM) (FIG. 7B) of PEM using SIM mode analysis.

Figure 8:
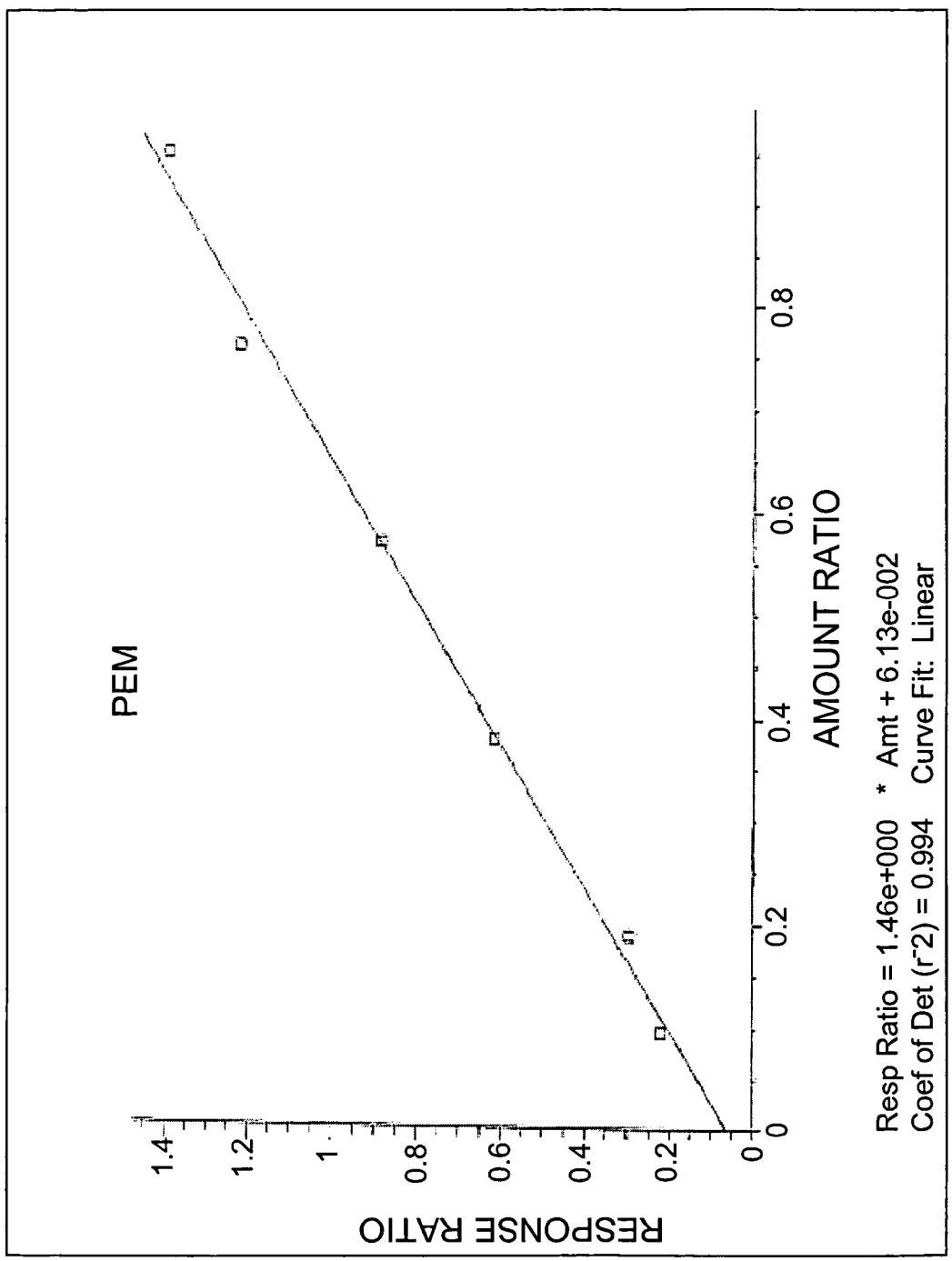
FIG. 8 depicts a standard calibration curve for the PY/GC/MS method described in Example 4.

In order to quantify the amount of ethyl methacrylate (EM) (and ultimately the amount of PEM) a standard curve is established for a range of PEM concentrations corresponding to the acceptable range of PEM in the efaproxiral-Na sample. Each sample is then analyzed in triplicate and the concentration of PEM is determined using the linear calibration curve prepared based on the results of PY/GC/MS of the deuterated PEM. Example 5 describes the preparation of a typical standard calibration curve for the quantification of PEM by PY/GC/MS. FIG. 8 depicts the standard calibration curve for the PY/GC/MS method described in Example 5.

The invention is further illustrated by the following non-limited examples. All scientific and technical terms have the meanings as understood by one with ordinary skill in the art. The specific examples that follow illustrate the methods in which the compositions of the invention may be prepared and are not to be construed as limiting the invention in sphere or scope. The methods may be adapted to variation in order to produce compositions embraced by this invention but not specifically disclosed. Further, variations of the methods to the produce the same compositions in somewhat different fashion will be evident to one skilled in the art.

Example 6 describes the purification of efaproxiral sodium (5) prepared according to the methods of Examples 1, 2 and 3 by filtration of the recrystallized product obtained from Example 3 through the following three filters: a polytetrafluoroethylene (PTFE) filter, a cellulose ester filter and a poly (vinylidene difluoride) (PVDF) filter. The results are set forth in Table 3. With reference to Table 3, it can be seen that PVDF filtration reduced the levels of PEM from about 55 ppm to about 9 ppm.

EXAMPLES

Materials. The following reactions were carried out in either Hastelloy 276®, SS (316) or glass-lined SS reactors. The Gas Chromatography/Mass Spectrometry was performed using a Hewlett Packard 5890 or 6890 Gas Chromatograph, interfaced with a 5971, 5972 or 5973 Mass Spectrometer; equipped with cryogenic cooling option, GC/MS ChemStation software, version A.03.00 or greater. Gas chromatography column, DB-5 Column 15 m×0.25 mm×0.25 μm, VWR.

Example 1

Preparation of 2-[4-((((3,5-dimethylphenyl)amino) carbonyl)methyl)phenoxy]-2-methyl propionic acid FIG. 3 illustrates a general five step reaction scheme for the preparation of 2-[4-((((3,5-dimethylphenyl)amino)carbonyl) methyl)phenoxy]-2-methyl propionic acid which is described in detail below.

Synthesis of Amidophenol (3)

With reference to FIG. 3, 4-hydroxyphenylacetic acid (200 kg) (2) was added to xylene (760 L) with stirring. To this mixture, 3,5-xylidine (3,5-dimethyl aniline) (178 L) (1) was added. The reaction mixture was heated to reflux and water was removed azeotropically as the reaction proceeded. Upon completion, the reaction mixture was distilled to provide amidophenol (3), which solidified upon cooling. To recrystallize, ethanol (1180 L) and methyl isobutyl ketone (MIBK) (56 L) were added to the solid and the mixture was refluxed until dissolution. Upon dissolution water was added (70° C., 490 L) and mixture was stirred and cooled slowly over 6 hours to about 0° C. The mixture was then stirred for at least one hour at this temperature. The mixture was then filtered, and the solid washed with 1:2 ethanol/water at 5° C., followed by a wash with xylene (452 L at 5° C.).

Synthesis of Efaproxiral Ethyl Ester (4)

Methyl isobutyl ketone (MIBK) (827 L) was added to the crystallized amidophenol (3) and the mixture was refluxed to azeotropically remove water. The reaction mixture was then cooled to below 70° C., and absolute ethanol (731 L) was added, followed by anhydrous potassium carbonate (668 kg) and ethyl 2-bromoisobutyrate (366 L). The reaction mixture was refluxed for at least 7 hours, then cooled to below 0° C. The mixture was filtered, and the solids were washed with MIBK such that the total volume of the wash plus the filtrate was 1208 L. The mixture was the distilled to remove the ethanol and the volume was adjusted with MIBK to about 2163 L. The MIBK mixture was extracted with dilute aqueous base (32 kg sodium bicarbonate in 604 L of water), followed aqueous acid (63 L in 572 liters of water, and water (3×700 L each). The mixture was then distilled to remove MIBK and cooled to about 35° C. Heptane (about 572 L) was added and the solution was stirred while additional heptane (approximately 1145 L) was slowly added over the course of one hour. The mixture was then cooled to about 12° C., stirred for at least 2 hours and then filtered. The solid, efaproxiral ethyl ester (4) was washed with heptane (318 L).

Synthesis of Efaproxiral Sodium (5)

Absolute ethanol (880 L) was first mixed with water (19 L), followed by the addition of sodium hydroxide (36 kg). This mixture was filtered, efaproxiral ethyl ester (4) was added and the reaction mixture was refluxed for at least 3 hours. Sodium hydroxide (10 N, 1 molar equivalent) was then added and reflux was maintained for at least 5 hours after the last addition. The mixture was then concentrated by distillation, and absolute ethanol (1056 L) was added. The water content was less than 0.5%. The reaction mixture was then cooled to about 40° C., then 35° C., and stirred for at least 2 hours. The mixture was then concentrated under vacuum to about 1408 L, cooled to about 10° C., and stirred for at least 5 hours. The mixture was then filtered and the solid, which consisted primarily of the sodium salt of 2-[4-((((3,5-dimethylphenyl) amino)carbonyl)methyl)phenoxy]-2-methyl propionic acid (efaproxiral sodium) (5), was washed with ethanol (282 L at 10° C.).

Example 2

Purification of Efaproxiral Sodium (5) by Extraction with MIBK

Purified water (1658 L) was added to the product (5) (325 kg) obtained using the method described in Example 1. The mixture was distilled under vacuum at a maximum temperature of 50° C. until about 423 L of solvent was removed. Another 423 L of purified water was then added and the aqueous solution was extracted with MIBK (390 L, below 30° C.). The organic phase was discarded, the aqueous phase was extracted again with MIBK (228 L, below 30° C.) and the organic phase was discarded.

Example 3

Purification of Efaproxiral Sodium (5) by Recrystallization with Acetone/Ethanol The sodium salt of efaproxiral (5) synthesized as described in Examples 1 and 2 in the aqueous solution was concentrated under vacuum at a maximum temperature of 50° C. to the maximum extraction of solvent, after which absolute ethanol (406 L) was added to provide a mixture having a water content of between 5 and 5.4%. The mixture was then cooled to about 47° C., acetone (975 L) was added and the mixture was stirred while maintaining the temperature. After crystallization, the mixture was stirred for at least one hour, after which an equal volume of acetone was added. The mixture was then slowly cooled to a temperature of about 15° C. and stirred for at least 5 hours. The crystals were collected on a filter and washed with acetone (146 L).

Example 4

Quantitation of trace poly-ethyl methacrylate impurity in 2-[4-((((3,5-dimethylphenyl)amino)carbonyl)methyl)phenoxy]-2-methyl propionic acid Described below is a method for measuring trace amounts of PEM impurity in 2-[4-((((3,5-dimethylphenyl)amino)carbonyl)methyl)phenoxy]-2-methyl propionic acid using pyrolysis/gas chromatography/mass spectrometry (PY/GC/MS). PY/GC/MS is useful when the analyte in question has a large molecular weight and is either semi-volatile or nonvolatile. As discussed in detail above, typically, the sample being analyzed is heated in a controlled manner to create reproducible pyrolytically-derived compound fragments, which are then analyzed by normal GC or GC/MS. In the instant case, when a sample containing trace amounts of PEM, is subjected to pyrolysis the monomer ethyl methacrylate (EM) is generated, which is accurately measured by GC or GC/MS. An internal standard, such as deuterated PEM in methanol/methylene chloride, is introduced to provide the required precision and accuracy in the analytical test. The deuterated PEM is differentiated from the analyte PEM by its greater mass units.

A 5 g sample of solid 2-[4-((((3,5-dimethylphenyl)amino)carbonyl)methyl)phenoxy]-2-methyl propionic acid sodium salt (5) was dissolved in methanol and a deuterated analog of PEM in methylene chloride was added to the solution as an internal standard. Additional methylene chloride was then added until a ratio of 40:60 methanol:methylene chloride was attained. The methylene chloride was required to solubilize the PEM released from the matrix. An aliquot of the sample was then placed into a prepared quartz tube packed with glass wool. After the solvent evaporated, the quartz tube was loaded into the pyrolysis unit and analyzed by PY/GC/MS using known methods. The PEM concentration in the sample was calculated using a linear calibration curve prepared based on the results of PY/GC/MS of the deuterated PEM as described in Example 5.

Example 5

Preparation of a Standard Calibration Curve for the Quantification of PEM by PY/GC/MS Three standard solutions were prepared and analyzed according to the method described in Example 4. Three additional standard solutions were also prepared in order to demonstrate that acceptable linearity exceeds both ends of the calibration range specified in the method. Table 2 shows the concentration of each standard analyzed. Calibration levels corresponding to those normally used in the method are indicated by an asterisk. The standard solutions were then analyzed from the lowest to the highest concentration and a concentration calibration curve was constructed by plotting the Amount Ratio (X-axis) vs. the Response Ratio (Y-axis) as follows.

The Amount Ratio (X-axis) is the concentration of PEM divided by the concentration of PEM-$d_5$ present in each standard solution. All concentrations are expressed as mass of compound sample analyzed, and are calculated by multiplying the concentrations shown in Table 2 (ng/µL) by the volume of standard solution analyzed (µL). In the instant case, the resulting units are ng in sample analyzed. Implicit in the use of the unit "ng/sample analyzed" is the assumption that the % transfer of material to the column is the same for both the internal standard and sample. The appropriateness of this assumption is demonstrated in recovery experiments.

The "Response Ratio" (Y-axis) is calculated by dividing the measured area of the PEM peak (m/z=99) by the measured area of the PEM-$d_5$ peak (m/z=104). A non-weighted least-squares linear regression is performed on the paired data points (the corresponding ratios for each standard) to determine the calibration plot's line equation (slope and y-intercept). To determine sample solution concentrations ("ng on-column"), the line equation is solved for PEM concentration (i.e. y=mx +b is solved for x) as shown in Equation 1:

$$[PEM] = \frac{\left[\left(\frac{\text{Area } PEM}{\text{Area } PEM\ d_5}\right) - (y\ \text{intercept})\right]}{\text{slope}} \times \text{internal standard concentration} \quad (1)$$

wherein
[PEM]=ng in sample analyzed concentration of PEM in sample solution analyzed
Area PEM=area of the m/z=99 (PEM) peak in the sample
Area PEM $d_5$=area of the m/z=104 (PEM-$d_5$) peak in the sample
y intercept=y-intercept of the calibration curve equation
slope=slope of the calibration curve equation and
internal standard concentration=concentration of PEM-$d_5$ in the sample.

To calculate concentration in the solid sample, the [PEM] result derived from Equation 1 is multiplied by the volume of sample solution analyzed (units of µL) and divided by the concentration of the solid sample in the sample solution (units of mg/µL). The result is a PEM concentration in ng PEM/mg efaproxiral-Na. This number can also be expressed as ppm.

The calculation shown in Equation 1 is generally described in general in: Hewlett-Packard MS ChemStation User's Guide for HP G1034C MS Chemstation Software, Hewlett-Packard Company, Publication number G1034-90043, First Edition, 2/93. The calculation is automatically performed by the MS Chemstation software for analyses involving internal standards. Using this procedure, a calibration curve plot for the six standards analyzed was constructed. The resulting calibration curve which is set forth in FIG. 8, resulted in an $R^2$ value of 0.994.

Example 6

Purification of Efaproxiral Sodium (5) by Filtration Through a poly(vinylidene difluoride) (PVDF) Filter Formulation of Efaproxiral-Na
A sample of 2-[4,-((((3,5-dimethylphenyl)amino)carbonyl)methyl)phenoxy]-2-methyl propionic acid sodium salt (efaproxiral-Na) prepared as described in Examples 1, 2 and 3 was analyzed for PEM as described in Example 5. The results from that analysis demonstrated a PEM content of 50.3±0.3 µg PEM/g efaproxiral-Na (50 ppm). This RSR 13-Na composition was then formulated for use as a drug product as follows: To a 1 L volumetric flask was added sodium chloride (2.25 g), anhydrous monobasic sodium phosphate (135 mg) and dibasic sodium phosphate, heptahydrate (7 mg), followed by approximately 800 mL of deionized water. The mixture was mixed until all of the solids had dissolved. To this solution was added efaproxiral-Na (21.3 g). The mixture was again mixed until all of the solids had dissolved. The pH of the resulting solution was then adjusted to approximately 7.9 using 0.1N HCl. Finally, the solution was diluted to volume using deionized water. The resulting solution represents a formulated efaproxiral drug product.

Analysis of the Formulated Efaproxiral-Na

To a 4 mL aliquot of the formulated efaproxiral drug product was added 20 μL of PEM-$d_5$ internal standard solution in a 13×100 mm test tube. The mixture was vortexed to homogeneity and frozen in a dry ice-isopropanol bath. The frozen sample was then lyophilized to dryness overnight. To the resulting lyophilized cake was added 400 μL of methanol followed by votexing. To this resulting mixture was added 600 μL of methylene chloride followed by vortexing. A representative sample of the prepared mixture was then centrifuged on a table-top centrifuge for five minutes. From the centrifuge tube, 5 μL of supernatant solution was transferred to a quartz tube for analysis by PY/GC/MS as described above. The determined value for PEM in the formulated drug product based on this analysis was 50.9±5.0 μg PEM/g efaproxiral-Na.

Purification of Formulated Efaproxiral-Na by PVDF Filtration

A sample of the formulated efaproxiral drug product (50 mL) prepared as described above, was placed into a 50 mL glass syringe. To the syringe was attached one of three 0.22 μm, 25 mm disposable syringe filters (3.9 cm² filter area) (as set forth in Table 3). The solution was then pushed through the selected filter at a rate of approximately 8 mL/min. The entire 50 mL of filtrate was collected in a clean glass container. A 4 mL homogeneous aliquot of filtrate for each filter type was then analyzed for PEM content as described above. The results of these filtration experiments are set forth in the Table 3.

The foregoing description is considered to be illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact composition and process shown or described above. Accordingly, all suitable modifications and equivalents may be resorted to falling within the scope of the invention as defined by the claims that follow.

TABLE 1

Related Impurities in RSR 13 Compositions

| Impurity | Short Name | Code | Structure |
|---|---|---|---|
| A | 3-monomethylanilino efaproxiral | 3MMRS13 | [structure] |
| B | α-desmethyl to COOH | DDMRS13 | [structure] |
| C | monomethyl α to COOH | DMRS13 | [structure] |
| D | Diacid | DA | [structure] |
| E | 3,4-dimethyl efaproxiral | 3,4DMRS13 | [structure] |

TABLE 1-continued

Related Impurities in RSR 13 Compositions

| Impurity | Short Name | Code | Structure |
|---|---|---|---|
| F | α-ethyl-efaproxiral | α-ethyl-efaproxiral | (structure) |
| G | 3,5-dimethylaniline | 3,5-DMA | (structure) |
| H | amidophenol | amidophenol | (structure) |
| I | efaproxiral ethyl ester | efaproxiral ethyl ester | (structure) |

TABLE 2

Calibration Standard Levels

| Standard Level | [PEM] (ng/μL) | [PEM-d5] (ng/μL) |
|---|---|---|
| 1 | 0.985 | 10.4 |
| 2 | 1.97* | 10.4 |
| 3 | 3.94* | 10.4 |
| 4 | 5.91 | 10.4 |
| 5 | 7.88* | 10.4 |
| 6 | 9.85 | 10.4 |

*Calibration levels corresponding to those typically used

TABLE 3

Filtration of Formulated Efaproxiral Drug Product

| Filter Composition | PEM (μg/g efaproxiral-Na) |
|---|---|
| No Filter | 55.6 |
| PTFE | 61.6 |
| Cellulose Esters | 15.6 |
| PVDF | 9.3 |

The invention claimed is:

1. A method for the preparation of a composition comprising an allosteric effector compound that is substantially free of polymeric impurities said method comprising the steps of:
   a) coupling a substituted aniline with 4-hydroxyphenylacetic acid to yield the corresponding substituted phenol;
   b) adding the product of step (a) to an alkyl ester halide to yield a substituted ethyl ester; and
   c) saponifying the substituted alkyl ester to provide the salt of the acid, wherein all steps are performed in a reaction vessel that does not, either in the reaction mixture or in the material constituting the reaction vessel itself, contain metals that promote the formation of polymeric byproducts, wherein said polymeric impurity is present in the composition at less than about 500 ppm.

2. The method of claim 1, wherein said polymeric impurity is selected from the group of compounds having the following structure:

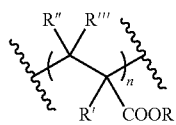

wherein
   R, R', R" and R'" are independently selected from the group consisting of substituted or unsubstituted $C_{1-12}$ alkyl group, hydrogen, halogen, a carboxylic acid or ester group, and a substituted or unsubstituted heteroaromatic group; and
   n is any number of units appropriate for a polymer of repeating units.

3. The method of claim 2, wherein R' is independently selected from a substituted or unsubstituted $C_{1-3}$ alkyl group and R is a methyl or ethyl group.

4. The method of claim 1, wherein said polymeric impurity is poly(ethyl methacrylate) (PEM).

5. The method of claim 1, wherein said polymeric impurity is present in the composition at less than about 200 ppm.

6. The method of claim 1, wherein said polymeric impurity is present in the composition at less than about 100 ppm.

7. The method of claim 1, wherein said polymeric impurity is present in the composition at less than about 80 ppm.

8. The method of claim 1, wherein said polymeric impurity is present in the composition at less than about 10 ppm.

9. The method of claim 1, wherein said reaction vessel is selected from the group consisting of glass lined stainless steel (SS), passivated stainless steel, Hastelloy.RTM. or similar alloys.

10. The method of claim 1, wherein said allosteric effector compound is selected from the group of compounds having the following formula:

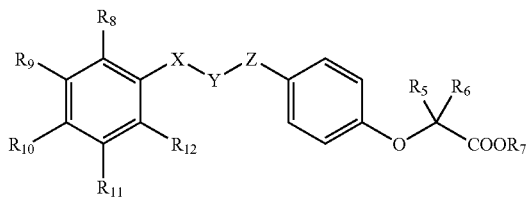

wherein
X and Z are independently selected from the group consisting of $CH_2$, CO, NH or O, and Y is selected from the group consisting of CO or NH, with the caveat that X, Y, and Z must all be different from each other;
$R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups, or alkyl moieties of part of an aliphatic ring connecting $R_5$ and $R_6$;
$R_7$ is a selected, from the group consisting of hydrogen, a cationic counterion, selected from the group consisting of sodium; potassium or ammonium, a metal, or a substituted or unsubstituted $C_{1-6}$ alkyl group; and
$R_{8-12}$ are independently selected from the group consisting of hydrogen, halogen, substituted or unsubstituted $C_{1-3}$ alkyl groups, or alkyl moieties of an aromatic or aliphatic ring incorporating two of the $R_{8-12}$ sites.

11. The method of claim 10, wherein said allosteric effector compound is selected from the group of compounds having the following chemical structure:

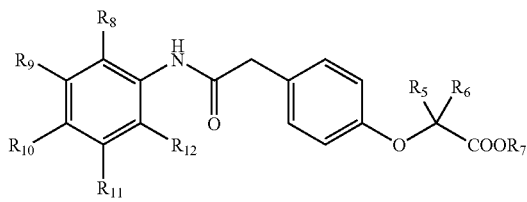

wherein
$R_5$ and $R_6$ are independently selected from the group consisting of hydrogen, halogen, substituted or unsubstituted $C_{1-12}$ alkyl groups, carboxylic acid and ester groups, substituted or unsubstituted aromatic or heteroaromatic groups or alkyl moieties of part of an aliphatic ring connecting $R_5$ and $R_6$;
$R_7$ is a selected from the group consisting of hydrogen, a cationic counterion, selected from the group consisting of sodium, potassium or ammonium, a metal, or a substituted or unsubstituted $C_{1-6}$ alkyl group; and
$R_{8-12}$ are independently selected from the group consisting of hydrogen, halogen, substituted or unsubstituted $C_{1-3}$ alkyl groups or alkyl moieties of an aromatic or aliphatic ring incorporating two of the $R_{8-12}$ sites.

12. The method of claim 11, wherein $R_5$ and $R_6$ are independently selected from H or $CH_3$ and $R_7$ is selected from hydrogen or a cationic counterion.

13. The method of claim 11, wherein said allosteric effector compound is 2-[4-((((3,5-dimethylphenyl)amino)carbonyl)methyl)phenoxy]-2-methyl propionic acid (efaproxiral) (5)

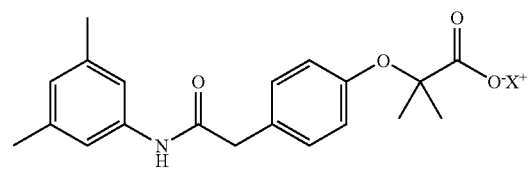

wherein X is selected from the group consisting of H or a cationic counterion selected from the group consisting of sodium, potassium or ammonium.

14. The method of claim 1, wherein said method further comprises extracting the product of step (c) with a solvent selected from the group consisting of methyl isobutyl ketone, isopropyl acetate, ethyl acetate, methyl ethyl ketone, chlorinated solvents selected from the group consisting of chloroform and methylene chloride at least once.

15. The method of claim 14, wherein said extraction is performed two times.

16. The method of claim 1, wherein said method further comprises recrystallization of the product of step (c) in an appropriate solvent.

17. The method of claim 16, wherein said solvent is selected from the group consisting of ethanol and acetone and mixtures of acetone/ethanol, acetone/methanol and ethanol/methanol/acetone/water.

18. The method of claim 1, wherein said method further comprises extracting the product of step (c) with an appropriate solvent, followed by recrystallization of the extracted product.

19. The method of claim 1, wherein said method further comprises extracting the product of step (c) with an appropriate solvent, followed by recrystallization of the extracted product and filtration of the recrystallized product.

20. The method of claim 19, wherein said filtration is performed using a polymeric filter selected from the group consisting of poly(vinylidene difluoride) (PVDF) or a cellulose ester filter.

21. The method of claim 20, wherein said polymeric filter is PVDF.

22. A method for preparing a composition of the allosteric effector compound efaproxiral-Na that is substantially free of polymeric impurities said method comprising the steps of:
a) reacting a solution of 4-hydroxyphenylacetic acid with 3,5-dimethylaniline to yield amidophenol;

b) reacting the product of step (a) with ethyl 2-bromoisobutyrate to yield the ethyl ester; and c) saponifiying the product of (b) to yield a carboxylic acid salt, wherein all steps are performed in a reaction vessel that does not, either in the reaction mixture or in the material constituting the reaction vessel itself, contain metals that promote the formation of polymeric byproducts wherein said polymeric impurity is present in the composition at less than about 500 ppm.

23. The method of claim 22, wherein said method further comprises extracting the product of step (c) with a solvent selected from the group consisting of methyl isobutyl ketone, isopropyl acetate, ethyl acetate, methyl ethyl ketone, chlorinated solvents selected from the group consisting of chloroform and methylene chloride at least once.

24. The method of claim 23, wherein said extraction is performed two times.

25. The method of claim 22, wherein said method further comprises recrystallization of the product of step (c) in an appropriate solvent.

26. The method of claim 25, wherein said solvent is selected from the group consisting of ethanol and acetone and mixtures of acetone/ethanol, acetone/methanol and ethanol/methanol/acetone/water.

27. The method of claim 22, wherein said method further comprises extracting the product of step (c) with an appropriate solvent, followed by recrystallization of the extracted product and filtration of the recrystallized product.

28. The method of claim 27, wherein said filtration is performed using a polymeric filter selected from the group consisting of PVDF or a cellulose ester filter.

29. The method of claim 28 wherein said polymeric filter is PVDF.

30. A method for the preparation of efaproxiral-Na (5) compound of formula that is substantially free of impurities, said method comprising the steps of:

a) reacting a solution of 4-hydroxyphenylacetic acid with 3,5-dimethylaniline to yield amidophenol;

b) reacting the product of step (a) with ethyl 2-bromoisobutyrate to yield the ethyl ester;

c) saponifiying the product of (b) to yield a carboxylic acid salt; and d) extracting the product of step (c) with an appropriate solvent at least one time, wherein all steps are performed in a reaction vessel that does not, either in the reaction mixture or in the material constituting the reaction vessel itself, contain metals that promote the formation of polymeric byproducts wherein said polymeric impurity is present in the composition at less than about 500 ppm.

31. The method of claim 30, wherein the impurity is a polymeric impurity.

32. The method of claim 31, wherein said polymeric impurity is present in the composition at less than about 100 ppm.

33. The product prepared according to the method of claim 30.

34. A method for the preparation of efaproxiral-Na (5) compound of formula that is substantially free of impurities, said method comprising the steps of:

a) reacting a solution of 4-hydroxyphenylacetic acid with 3,5-dimethylaniline to yield amidophenol;

b) reacting the product of step (a) with ethyl 2-bromoisobutyrate to yield the ethyl ester;

c) saponifiying the product of (b) to yield a carboxylic acid salt;

d) extracting the product of step (c) with an appropriate solvent at least one time, and e) recrystallizing the product of step (d) in an appropriate solvent, wherein all steps are performed in a reaction vessel that does not, either in the reaction mixture or in the material constituting the reaction vessel itself, contain metals that promote the formation of polymeric byproducts wherein said polymeric impurity is present in the composition at less than about 500 ppm.

35. The method of claim 34, wherein the solvent of step (d) is MIBK and the solvent of step (e) is selected from ethanol and/or acetone.

36. The method of claim 34, wherein said polymeric impurity is present in the composition at less than about 100 ppm.

37. The product prepared according to the method of claim 34.

38. A method for the preparation of efaproxiral-Na (5) compound of formula that is substantially free of impurities, said method comprising the steps of:

a) reacting a solution of 4-hydroxyphenylacetic acid with 3,5-dimethylaniline to yield amidophenol;

b) reacting the product of step (a) with ethyl 2-bromoisobutyrate to yield the ethyl ester;

c) saponifiying the product of (b) to yield a carboxylic acid salt;

d) extracting the product of step (c) with an appropriate solvent at least one time;

e) recrystallizing the product of step (d) in an appropriate solvent; and f) filtering the product of step (e) with a filter that removes polymeric impurities, wherein all steps are performed in a reaction vessel that does not, either in the reaction mixture or in the material constituting the reaction vessel itself, contain metals that promote the formation of polymeric byproducts wherein said polymeric impurity is present in the composition at less than about 500 ppm.

39. The method of claim 38, wherein the solvent of step (d) is MIBK, the solvent of step (e) is selected from ethanol and/or acetone and the polymeric filter of step (f) is PVDF.

40. The method of claim 38, wherein the solvent of step (d) is MIBK, the solvent of step (e) is selected from ethanol and/or acetone and the polymeric filter of step (f) is modified cellulose.

* * * * *